(12) United States Patent
Larsson et al.

(10) Patent No.: US 7,430,322 B1
(45) Date of Patent: Sep. 30, 2008

(54) PARTICLE SHAPE CHARACTERIZATION FROM 2D IMAGES

(75) Inventors: Mats I. Larsson, Sunnyvale, CA (US);
Cetin Kilic, Mountain View, CA (US);
Ariana Zimbouski, Berkeley, CA (US);
Juan Cai, Fremont, CA (US)

(73) Assignee: Nanostellar, Inc., Redwood City, CA (US)

( * ) Notice: Subject to any disclaimer, the term of this patent is extended or adjusted under 35 U.S.C. 154(b) by 499 days.

(21) Appl. No.: 11/167,517

(22) Filed: Jun. 27, 2005

Related U.S. Application Data

(63) Continuation-in-part of application No. 11/120,462, filed on May 2, 2005.

(51) Int. Cl.
G06K 9/46 (2006.01)
(52) U.S. Cl. .............. 382/203; 382/133; 382/204; 382/224; 382/285
(58) Field of Classification Search ......... 382/133, 382/154, 181, 203, 224, 225, 285
See application file for complete search history.

(56) References Cited

U.S. PATENT DOCUMENTS

| | | | | |
|---|---|---|---|---|
| 5,671,343 | A * | 9/1997 | Kondo et al. | 345/419 |
| 6,049,381 | A * | 4/2000 | Reintjes et al. | 356/335 |
| 6,168,775 | B1 | 1/2001 | Zhou et al. | |
| 6,522,781 | B1 * | 2/2003 | Norikane et al. | 382/203 |
| 6,535,836 | B1 * | 3/2003 | Grace | 702/179 |
| 6,552,781 | B1 * | 4/2003 | Rompel et al. | 356/71 |
| 6,746,597 | B2 | 6/2004 | Zhou et al. | |
| 7,269,285 | B2 * | 9/2007 | Bober et al. | 382/190 |
| 2007/0127816 | A1 * | 6/2007 | Balslev et al. | 382/181 |

OTHER PUBLICATIONS

Abou-Chakra, H., J. Baxter, and U. Tüzün. "Three-dimensional particle shape descriptors for computer simulation of non-spherical particulate assemblies." Advanced Powder Technology. 15/1(2004): 63-77.*

Liu, B., and P. Wang. "Recognition of 3D Objects from 2D Images—Some Issues." SSPR 1996 (1996): 240-250.*

Wang, Patrick S. P.. "High Level Representation and Recognition of 3D Objects From 2D Images." (1997) 1-27. Dec. 31, 2007 <High Level Representation and Recognition of 3D Objects From 2D Images>.*

(Continued)

*Primary Examiner*—Samir A. Ahmed
*Assistant Examiner*—Michael A Newman
(74) *Attorney, Agent, or Firm*—Patterson & Sheridan, L.L.P.

(57) ABSTRACT

The size distributions corresponding to the three-dimensional (3D) shapes of particles are estimated from a 3D-to-2D projection matrix and a two-dimensional (2D) image of the particles that is obtained using TEM. Two different methods to generate a 3D-to-2D projection matrix are described. The first method determines the matrix coefficients assuming equal probability for all high-symmetry projections. The second method employs a large set of 3D-to-2D projection matrices with randomly generated coefficients satisfying the high-symmetry projection constraint. The second method is a general method to determine 3D-to-2D projection matrices based on the assumption that certain high-symmetry projections are present for the system under investigation.

6 Claims, 22 Drawing Sheets

OTHER PUBLICATIONS

Abou-Chakra, et al., "Three-dimensional particle shape descriptiors for computer simulation of non-spherical particulate assemblies," *Advanced Powder Technology*, 15/1(2004): 63-77.*

U.S. Appl. No. 11/016,578, filed Dec. 17, 2004, Cai et al.

Jingyue Liu, "Advanced Electron Microscopy Characterization of Nanostructured Heterogeneous Catalysts," *Microsc. Microanal.*, 2004, vol. 10: pp. 55-76.

L.B. Kiss et al., "New Approach to the Origin of Lognormal Size Distributions of Nanoparticles," *Nanotechnology*, 1999, vol. 10: pp. 25-28.

Temer S. Ahmadi et al., "Shape-Controlled Synthesis of Colloidal Platinum Nanoparticles," *Science*, Jun. 1996, vol. 272: pp. 1924-1926.

Yugang Sun et al., "Shape-Controlled Synthesis of Gold and Silver Nanoparticles," *Science*, Dec. 2002, vol. 298: pp. 2176-2179.

Amanda Crowell, "Shaping Nanoparticles," *Research Horizons: Georgia Institute of Technology*, 1996, vol. 14(2).

C.G. Granqvist et al., "Ultrafine Metal Particles," *Journal of Applied Physics*, May 1976, vol. 47(5): pp. 2200-2219.

* cited by examiner

FIG. 2

| 2D shape \ 3D shape | Tetragon (Tet) Tet from cc | Tetragon (Tet) Tet from tt | Round (R) R from cc | Round (R) R from tt | Round (R) R from to | Triangle or Unique (Tri) Tri from tt |
|---|---|---|---|---|---|---|
| Cube Cub-octahedron (cc) | 0.34 | 0 | 0.66 | 0 | 0 | 0 |
| Tetrahedron Truncated Tetrahedron (tt) | 0 | 0.09 | 0 | 0.09 | 0 | 0.82 |
| Truncated Octahedron (to) | 0 | 0 | 0 | 0 | 1.00 | 0 |

FIG. 4

| $N_L$ | $N_U$ | g1(N) | g2(N) | g3(N) | g4(N) | g5(N) | g6(N) |
|---|---|---|---|---|---|---|---|
| 1 | 100 | | | | | | |
| 101 | 200 | | | | | | |
| 201 | 300 | | | | | | |
| 301 | 400 | | | | | | |
| 401 | 500 | | | | | | |
| 501 | 600 | | | | | | |
| 601 | 700 | | | | | | |
| 701 | 800 | | | | | | |
| 801 | 900 | | | | | | |
| 901 | 1000 | | | | | | |
| 1001 | 1100 | | | | | | |
| 1101 | 1200 | | | | | | |
| 1201 | 1300 | | | | | | |
| 1301 | 1400 | | | | | | |
| 1401 | 1500 | | | | | | |
| 1501 | >1501 | | | | | | |

FIG. 9

| 2D shape \ 3D shape | Tetragon (Tet) Tet from cc | Tetragon (Tet) Tet from tt | Round (R) R from cc | Round (R) R from tt | Round (R) R from to | Triangle or Unique (Tri) Tri from tt |
|---|---|---|---|---|---|---|
| Cube Cub-octahedron (cc) | α1 | 0 | α2 | 0 | 0 | 0 |
| Tetrahedron Truncated Tetrahedron (tt) | 0 | β1 | 0 | β2 | 0 | β3 |
| Truncated Octahedron (to) | 0 | 0 | 0 | 0 | 1.00 | 0 |

FIG. 14

| 3D shape \ 2D shape | Triangle | Square | Rectangle | Round | Rhombus | Unique |
|---|---|---|---|---|---|---|
| Tetrahedron | α1 | α2 | | | | |
| Cube | | β2 | β3 | β4 | | |
| Octahedron | | χ2 | χ3 | χ4 | χ5 | |
| Truncated Tetrahedron | | | | δ4 | | δ6 |
| Cub-octahedron | | ε2 | | ε4 | | |
| Truncated Octahedron | | | | φ4 | | |

PARTICLE SHAPE CHARACTERIZATION FROM 2D IMAGES

RELATED APPLICATION

This application is a continuation-in-part of application Ser. No. 11/120,462, filed May 2, 2005, entitled "Particle Shape Characterization from 2D Images."

BACKGROUND OF THE INVENTION

1. Field of the Invention

The present invention generally relates to physical characterization of particles and, more particularly, to characterization of three-dimensional (3D) shapes of nanometer-sized particles from two-dimensional (2D) images of the particles.

2. Description of the Related Art

The performance of heterogeneous catalysts is highly dependent on their physical properties, including pore size, surface area and morphology of the carrier, and size and weight of the active catalytic components. As a result, techniques for characterizing the physical properties of heterogeneous catalysts become important when assessing their performance. An article by J. Liu, entitled "Advanced Electron Microscopy Characterization of Nanostructured Heterogeneous Catalysts," Microscopy and Microanalysis, Vol. 10, pp. 55-76 (2004), discusses various advanced electron microscopy techniques used in characterizing model and heterogeneous catalysts, including transmission electron microscopy (TEM), scanning transmission electron microscopy (STEM), and scanning electron microscopy (SEM).

It is understood in the art that the shape of the catalyst surface on which catalysis is carried out plays an important role in determining the performance of the heterogeneous catalyst. U.S. Pat. No. 6,746,597, for example, teaches that the crystal surface [111] of a noble metal catalyst material is selective for hydrogenation and dehydrogenation reactions. However, as the size of the catalyst materials have decreased to nanometer levels, it has become difficult to characterize the shape of the catalyst materials.

There have been some attempts to characterize the shapes of catalyst materials at the nanometer levels. An article by T. Ahmadi et al. entitled, "Shape-Controlled Synthesis of Colloidal Platinum Nanoparticles," Science, Vol. 272, pp. 1924-1926 (June 1996), discloses a method in which 3D shapes of the particles were determined by tilting the samples in the TEM. An article by Y. Sun et al. entitled, "Shape-Controlled Synthesis of Gold and Silver Nanoparticles," Science, Vol. 298, pp. 2176-2179 (December 2002), discloses another method in which 3D shapes of the particles were determined by taking an SEM image of a sample at a tilting angle of 20°.

The methods for characterizing the shape of catalyst materials described above have some limitations. The method employed by T. Ahmadi et al. appears to require tilting and enlargement of each of the nanoparticles being analyzed. Such a process would be too time consuming in practice, especially when a large number of nanoparticles that are less than 5 nm are present. The method employed by Y. Sun et al. addresses tilting of very large nanoparticles (~100 nm) that resemble almost ideal metal cubes. For much smaller size nanoparticles having a number of different non-ideal possible shapes, shape characterization becomes very difficult with existing methods. In fact, the article by J. Liu explains that even for model supported nanoparticles, it is difficult, if not impossible, to obtain statistically meaningful results on the shape distributions of the metal nanoparticles.

SUMMARY OF THE INVENTION

The present invention provides a technique of characterizing 3D shapes of particles from 2D images of the particles. Using the characterized 3D shapes, a more accurate size distribution of nanoparticles can be obtained, especially when TEM images yield a somewhat small sampling set of nanoparticles. Also, the 3D shape information of the nanoparticles can be used in computer models for estimating chemical softness of the nanoparticles.

According to one embodiment, a 2D image of a batch of nanoparticles is obtained using a TEM and the 2D shapes of the nanoparticles are determined from the 2D image. The nanoparticles are classified into one of three 2D shape classes: triangle, tetragon and round, and one of three 3D shape classes. Based on the number of nanoparticles having the 2D triangle shape, the number of nanoparticles that are in the first of the three 3D shape classes is calculated. Based on the number of nanoparticles having the 2D triangle shape and the number of nanoparticles having the 2D tetragon shape, the number of nanoparticles that are in the second of the three 3D shape classes is calculated. Based on the number of nanoparticles having the 2D triangle shape, the number of nanoparticles having the 2D tetragon shape and the number of nanoparticles having the 2D round shape, the number of nanoparticles that are in the third of the three 3D shape classes is calculated.

According to another embodiment, a 2D image of a batch of nanoparticles is obtained using a TEM and the 2D shapes of the nanoparticles are determined from the 2D image. Six size distributions are determined from the nanoparticles. The first size distribution is derived from the nanoparticles having the 2D triangle shape. The second and third size distributions are derived from the nanoparticles having the 2D tetragon shape. The fourth, fifth and sixth size distributions are derived from the nanoparticles having the 2D round shape. Based on these six size distributions, three size distributions, each of which corresponds to one of three 3D shape classes, are estimated. The 3D shape classes include a first 3D shape class including a tetrahedron shape and a truncated tetrahedron shape, a second 3D shape class including a cube shape and a cub-octahedron shape, and a third 3D shape class including a truncated octahedron shape.

In the derivation of the number of nanoparticles having particular 3D shapes and the size distributions corresponding to particular 3D shapes, a 3D-to-2D projection matrix is used. The 3D-to-2D projection matrix defines the relationships between various 2D shapes and various 3D shapes, and each matrix entry represents the probability of having a 2D projection corresponding to that matrix cell from a 3D shape corresponding to that matrix cell. In some embodiments, a single set of fixed values is used in defining the relationships between the 2D shapes and the 3D shapes specified in the 3D-to-2D projection matrix. In other embodiments where a single set approach is not as applicable, multiple sets of fixed values that are derived based on randomly generated values are used. The method using randomly generated values is a general approach that can be applied to derive any 3D-to-2D projection matrix based on the assumption that certain high-symmetry 3D-to-2D projections are present for the system under investigation.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 2 shows the association of 2D shapes of a nanoparticle with various 3D shapes;

FIG. 4 is a table used in determining size distributions corresponding to 2D shapes;

FIG. 9 shows the relationships between various 2D shapes and various 3D shapes, where the relationships are defined with variables;

FIG. 14 shows an expanded 3D-to-2D projection matrix that shows the variable relationships between six different 2D shape classes and six different 3D shape classes.

DETAILED DESCRIPTION

Figure 1:
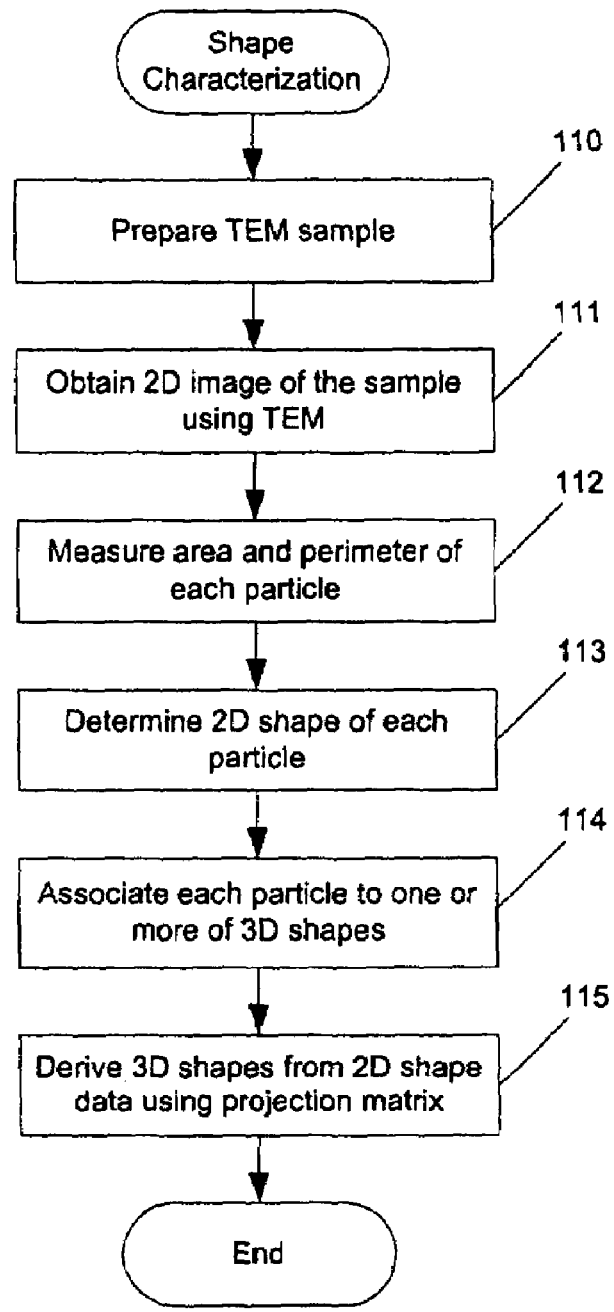
FIG. 1 is a flow diagram illustrating the 3D shape characterization method according to a first embodiment of the invention.

A shape characterization method according to a first embodiment of the invention is illustrated in the flow diagram of FIG. 1. In Step 110, a TEM sample of a batch of nanoparticles is prepared. For this step, the TEM sample preparation method disclosed in U.S. patent application Ser. No. 11/016,578, entitled "Method of Preparing Nanoparticle Samples," filed Dec. 17, 2004, incorporated by reference herein in its entirety, may be used. A TEM image of the sample is then obtained (Step 111). In Step 112, the area and the perimeter of each nanoparticle appearing in the TEM image is measured. Then, in Step 113, the 2D shape of each nanoparticle appearing in the TEM image is determined. The 2D shape is determined to be one of the following major types: tetragon, round, and triangle. The 2D shape determination of a nanoparticle may be performed visually from the TEM image or based on the form factor of the nanoparticle. The form factor of a nanoparticle is derived from the measured area (A) and the measured perimeter (P) of the nanoparticle. The form factor is defined as $4\pi*A/P^2$, which can also be expressed in terms of the harmonic parameter, h, as $2\pi*h/P$, where $h=2A/P$. The form factor by its definition represents the similarity between 2D shapes and circles, which have a form factor of exactly 1. Nanoparticles having form factors less than or equal to 0.75 are classified as triangles. Nanoparticles having form factors greater than or equal to 0.85 are classified as round. Nanoparticles having form factors between 0.75 and 0.85 are classified as tetragons.

In Step 114, each nanoparticle appearing in the TEM image is associated with one or more 3D shapes. The association of a nanoparticle having a particular 2D shape with one or more of the 3D shapes is shown in FIG. 2. The matrix shown in FIG. 2 is referred to as a 3D-to-2D projection matrix. The association is made based on expected 2D projections of nanoparticles having various 3D shapes. When there is more than one possible 2D projection, weight factors are assigned to each of the possible 2D projections, such that the sum of the weight factors for any one 3D shape is one. The weight factors represent the probability of having a particular 2D projection among all possible projections of the 3D shapes. For example, the probability of having a 2D tetragon shape projected from a cube shape and a cub-octahedron shape is 34%, and that of a 2D round shape projected from a cube shape and a cub-octahedron shape is 66%.

The 3D shapes include a 3D tt shape, which is a tetrahedron shape or a truncated tetrahedron shape, a 3D cc shape, which is a cube shape or a cub-octahedron shape, and a 3D to shape, which is a truncated octahedron shape. Each nanoparticle having a 2D triangle shape is associated with a 3D tt shape. Each nanoparticle having a 2D square shape is associated with a 3D cc shape and a 3D tt shape. Each nanoparticle having a 2D round shape is associated with a 3D cc shape, a 3D tt shape and a 3D to shape.

In Step 115, 3D shapes of the nanoparticles in the batch are derived from their 2D shapes based on the relationships between 3D shapes and 2D shapes set forth in the projection matrix. The equations for deriving the 3D shapes based on the 2D shape data are shown below:

$$M_{cc} = \frac{1}{0.34}\left(M^{Tet} - \frac{0.09}{0.82}M^{Tri}\right)$$

$$M_{tt} = \frac{1}{0.82}M^{Tri}$$

$$M_{to} = M^R - \frac{0.66}{0.34}M^{Tet} + \left(\frac{0.32}{0.34} \times \frac{0.09}{0.82}\right)M^{Tri}$$

where $M_{cc}$, $M_{tt}$ and $M_{to}$ represent the number of nanoparticles having 3D cc, tt and to shapes, respectively; and $M^{Tet}$, $M^R$ and $M^{Tri}$ are measured values that represent the number of nanoparticles having the 2D tetragon, round and triangle shapes, respectively. Since $M_{cc}$, $M_{tt}$ and $M_{to}$ cannot be less than zero, the above equations are valid so long as the measured values of $M^{Tet}$, $M^R$ and $M^{Tri}$ meet the following inequalities:

$$M^{Tet} > \frac{0.09}{0.82}M^{Tri}$$

$$M^R > \frac{0.66}{0.34}M^{Tet} - \left(\frac{0.32}{0.34} \times \frac{0.09}{0.82}\right)M^{Tri}$$

Figure 3:
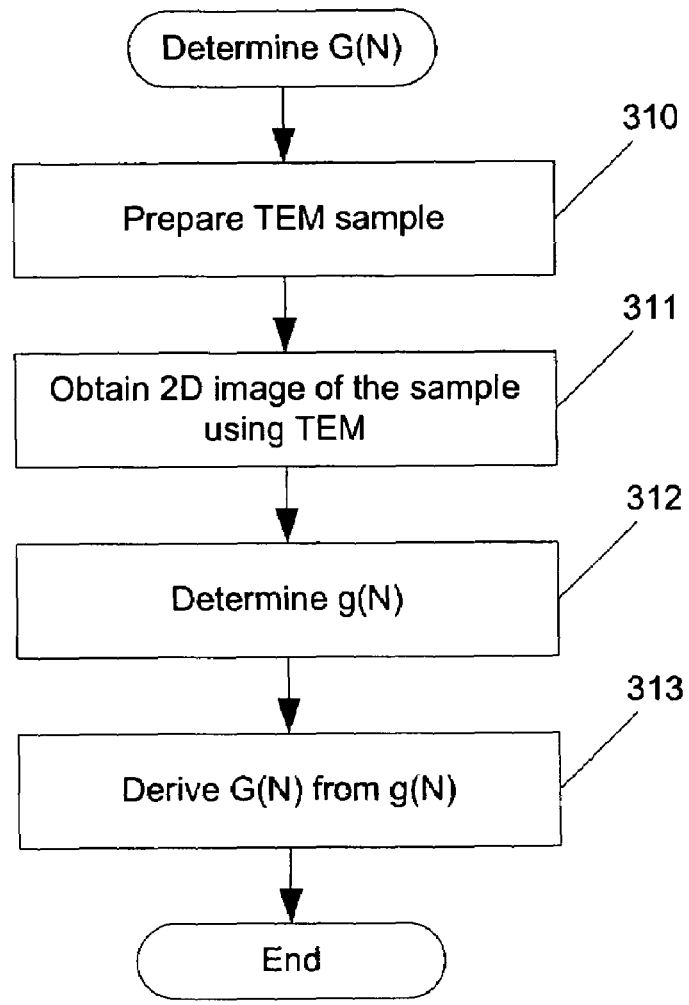
FIG. 3 is a flow diagram illustrating the 3D shape characterization method according to a second embodiment of the invention.

FIG. 3 illustrates a shape characterization method according a second embodiment of the invention. In this method, three distributions, one each for the 3D cc shape ($G_{cc}$), 3D tt shape ($G_{tt}$), and 3D to shape ($G_{to}$), that are defined with respect to the number of atoms (N), are determined from six distributions (g1, g2, g3, g4, g5 and g6), that are defined with respect to the number of atoms (N), based on the following matrix equation:

$$\{G\}=[CP']\times\{g\}$$

where:

$$\{G\} = \begin{Bmatrix} G_{cc}(N) \\ G_{tt}(N) \\ G_{to}(N) \end{Bmatrix};$$

$$\{g\} = \begin{Bmatrix} g_1(N) \\ g_2(N) \\ g_3(N) \\ g_4(N) \\ g_5(N) \\ g_6(N) \end{Bmatrix};$$

$$[CP'] = \begin{bmatrix} CP(1,1) & 0 & CP(1,3) & 0 & 0 & 0 \\ 0 & CP(2,2) & 0 & CP(2,4) & 0 & 1 \\ 0 & 0 & 0 & 0 & CP(3,5) & 0 \end{bmatrix};$$

$$CP(1,1) = 1 - \frac{0.09}{0.82}\frac{M^{Tri}}{M^{Tet}};$$

$$CP(1,3) = \frac{0.66}{0.64}\left(\frac{M^{Tet}}{M^R} - \frac{0.09}{0.82}\frac{M^{Tri}}{M^R}\right);$$

$$CP(2,2) = \frac{0.09}{0.82}\frac{M^{Tri}}{M^{Tet}};$$

$$CP(2,4) = \frac{0.09}{0.82}\frac{M^{Tri}}{M^R}; \text{ and}$$

$$CP(3,5) = 1 - \frac{0.66}{0.34}\frac{M^{Tet}}{M^R} + \frac{0.09}{0.82}\frac{0.32}{0.34}\frac{M^{Tet}}{M^R},$$

and where $M^{Tet}$, $M^R$ and $M^{Tri}$ are measured values that represent the total number of nanoparticles having the 2D tetragon, round and triangle shapes, respectively. In order for the matrix equation, $\{G\}=[CP']\times\{g\}$, to hold, the contributions to $\{G\}$ by $\{g\}$ must be greater than zero. It then follows that the measured values of $M^{Tet}$, $M^R$ and $M^{Tri}$ must meet the same inequalities as above:

$$M^{Tet} > \frac{0.09}{0.82}M^{Tri}$$

$$M^R > \frac{0.66}{0.34}M^{Tet} - \left(\frac{0.32}{0.34}\times\frac{0.09}{0.82}\right)M^{Tri}$$

In Step 310, a TEM sample of a batch of nanoparticles is prepared. For this step, the TEM sample preparation method disclosed in U.S. patent application Ser. No. 11/016,578 may be used. A TEM image of the sample is then obtained (Step 311). In Step 312, the six distributions (g1(N), g2(N), g3(N), g4(N), g5(N) and g6(N)) are determined in discrete form. FIG. 4 is a table used in deriving the six distributions in discrete form.

The g1(N) distribution is derived from the nanoparticles having the 2D triangle shape, and based on the knowledge that the 2D triangle shape is associated with a 3D tt shape. The value corresponding to g1($N_L$->$N_U$) represents the number of nanoparticles having the 2D triangle shape that have a number of atoms, as calculated from the 2D area of the nanoparticle and the associated 3D tt shape of the nanoparticle, that fall within the range defined by $N_L$ and $N_U$.

The g2(N) and g3(N) distributions are derived from the nanoparticles having the 2D tetragon shape, and based on the knowledge that the 2D tetragon shape is associated with either a 3D cc shape or a 3D tt shape. The value corresponding to g2($N_L$->$N_U$) represents the number of nanoparticles having the 2D tetragon shape that have a number of atoms, as calculated from the 2D area of the nanoparticle and the associated 3D cc shape of the nanoparticle, that fall within the range defined by $N_L$ and $N_U$. The value corresponding to g3($N_L$->$N_U$) represents the number of nanoparticles having the 2D tetragon shape that have a number of atoms, as calculated from the 2D area of the nanoparticle and the associated 3D tt shape of the nanoparticle, that fall within the range defined by $N_L$ and $N_U$.

The g4(N), g5(N) and g6(N) distributions are derived from the nanoparticles having the 2D round shape, and based on the knowledge that the 2D round shape is associated with a 3D cc shape or a 3D tt shape or a 3D to shape. The value corresponding to g4($N_L$->$N_U$) represents the number of nanoparticles having the 2D tetragon shape that have a number of atoms, as calculated from the 2D area of the nanoparticle and the associated 3D cc shape of the nanoparticle, that fall within the range defined by $N_L$ and $N_U$. The value corresponding to g5($N_L$->$N_U$) represents the number of nanoparticles having the 2D tetragon shape that have a number of atoms, as calculated from the 2D area of the nanoparticle and the associated 3D tt shape of the nanoparticle, that fall within the range defined by $N_L$ and $N_U$. The value corresponding to g6($N_L$->$N_U$) represents the number of nanoparticles having the 2D tetragon shape that have a number of atoms, as calculated from the 2D area of the nanoparticle and the associated 3D to shape of the nanoparticle, that fall within the range defined by $N_L$ and $N_U$.

Figure 5:
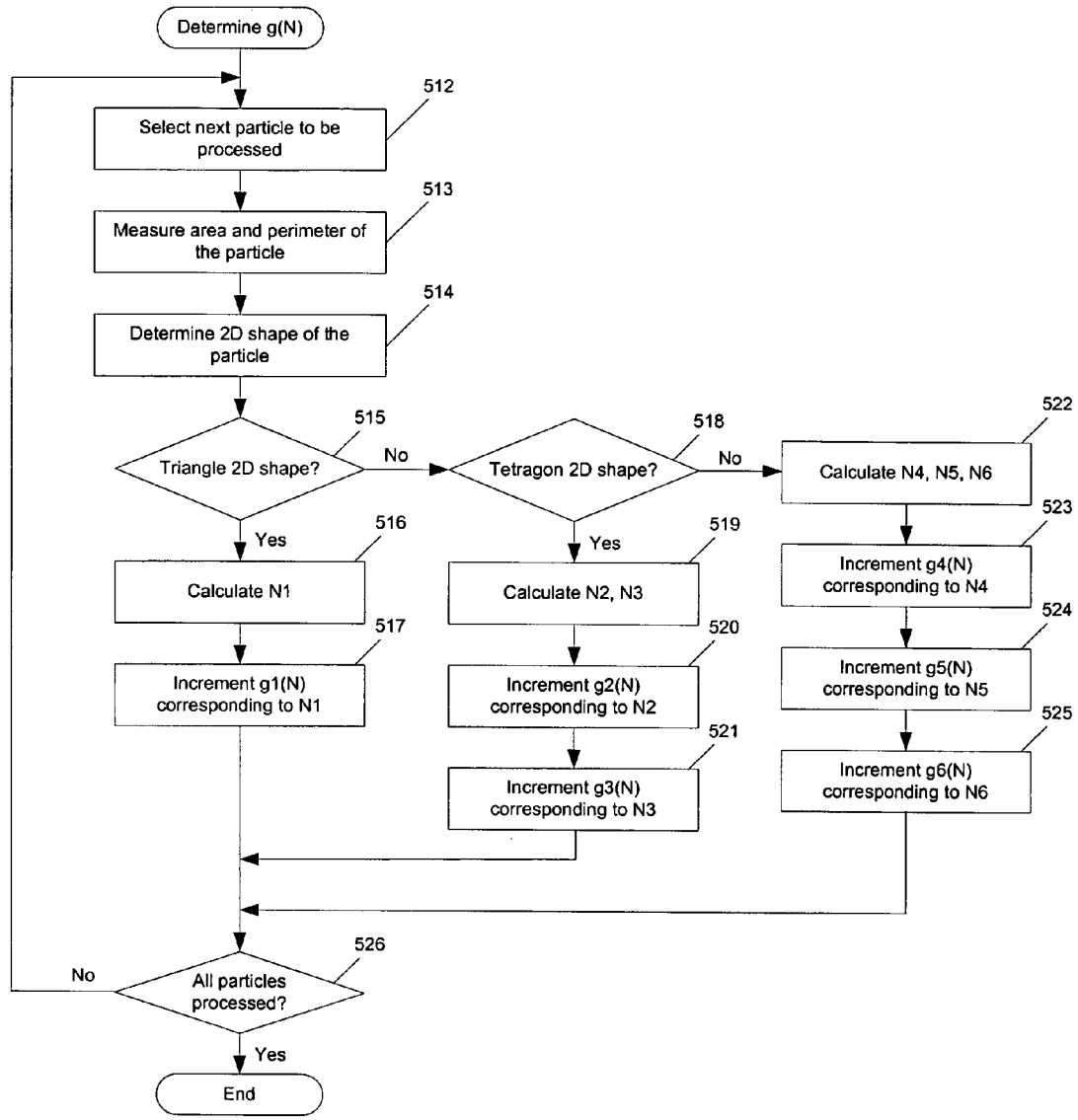
FIG. 5 is a flow diagram illustrating the method of determining the size distributions corresponding to 2D shapes.

FIG. 5 illustrates Step 312 in additional detail. In Steps 512-526, the nanoparticles appearing in the TEM image are processed one at a time. In Step 526, a check is made to see if all nanoparticles have been processed. If all nanoparticles have been processed, the process ends. If not, the process returns to Step 512, where the next nanoparticle to be processed is selected. In Step 513, the area (A) and the perimeter (P) of the nanoparticle selected in Step 512 are measured, and in Step 514, its 2D shape is determined. The 2D shape is determined to be one of the following major types: tetragon, round, and triangle. The 2D shape determination of a nanoparticle may be performed visually from the TEM image or based on the form factor of the nanoparticle, in the same manner as in Step 113 of the first embodiment.

If the 2D shape is determined to be a triangle in Step 515, Steps 516-517 are carried out. According to the projection matrix of FIG. 2, the 2D triangle shape is associated with the 3D tt shape, so in Step 516, the number of atoms in the nanoparticle determined to have the 2D triangle shape in Step 515 is calculated based on this association. The number of atoms, N1, is calculated based on the crystal structure of the element constituting the nanoparticle, its area (A), and the associated 3D shape. For a platinum nanoparticle having the associated 3D tt shape, N1=0.040*$A^{3/2}$. In Step 517, the g1($N_L$->$N_U$) value corresponding to N1 is incremented. Step 526 is then executed to see if all nanoparticles have been processed. If all nanoparticles have been processed, the process ends. If not, the process returns to Step 512, where the next nanoparticle to be processed is selected.

If the 2D shape is determined to be a tetragon in Step 518, Steps 519-521 are carried out. According to the projection matrix of FIG. 2, the 2D tetragon shape is associated with the 3D cc shape or the 3D tt shape, so in Step 519, the number of atoms in the nanoparticle determined to have the 2D tetragon shape in Step 518 is calculated twice, once for the association with the 3D cc shape (N2) and once for the association with the 3D tt shape (N3). The number of atoms is calculated based on the crystal structure of the element constituting the nanoparticle, its area (A), and the associated 3D shape. For a platinum nanoparticle having the associated 3D cc shape, $N2=0.050*A^{3/2}$. For a platinum nanoparticle having the associated 3D tt shape, $N3=0.023*A^{3/2}$. In Step 520, the $g2(N_L->N_U)$ value corresponding to N2 is incremented, and in Step 521, the $g3(N_L->N_U)$ value corresponding to N3 is incremented. Step 526 is then executed to see if all nanoparticles have been processed. If all nanoparticles have been processed, the process ends. If not, the process returns to Step 512, where the next nanoparticle to be processed is selected.

If the 2D shape is determined to be neither a triangle nor a tetragon, it is determined that the 2D shape is round and Steps 522-525 are carried out. According to the projection matrix of FIG. 2, the 2D round shape is associated with the 3D cc shape or the 3D tt shape or the 3D to shape, so in Step 522, the number of atoms in the nanoparticle determined to have the 2D tetragon shape in Step 518 is calculated three times, once for the association with the 3D cc shape (N4) and once for the association with the 3D tt shape (N5) and once for association with the 3D to shape. The number of atoms is calculated based on the crystal structure of the element constituting the nanoparticle, its area (A), and the associated 3D shape. For a platinum nanoparticle having the associated 3D cc shape, $N4=0.045*A^{3/2}$. For a platinum nanoparticle having the associated 3D tt shape, $N5=0.028*A^{3/2}$. For a platinum nanoparticle having the associated 3D to shape, $N6=0.036*A^{3/2}$. In Step 523, the $g4(N_L->N_U)$ value corresponding to N4 is incremented. In Step 524, the $g5(N_L->N_U)$ value corresponding to N5 is incremented. In Step 525, the $g6(N_L->N_U)$ value corresponding to N6 is incremented. Step 526 is then executed to see if all nanoparticles have been processed. If all nanoparticles have been processed, the process ends. If not, the process returns to Step 512, where the next nanoparticle to be processed is selected.

Figure 6A:
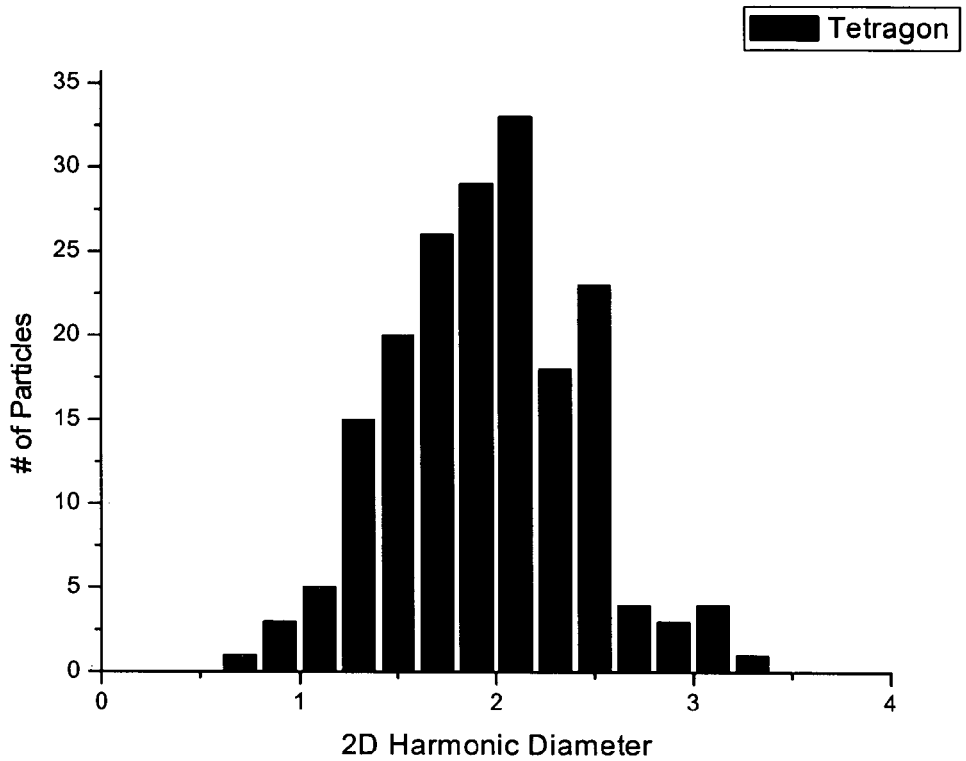
FIGS. 6A-D shows size distributions corresponding to 2D shapes.
Figure 6B:
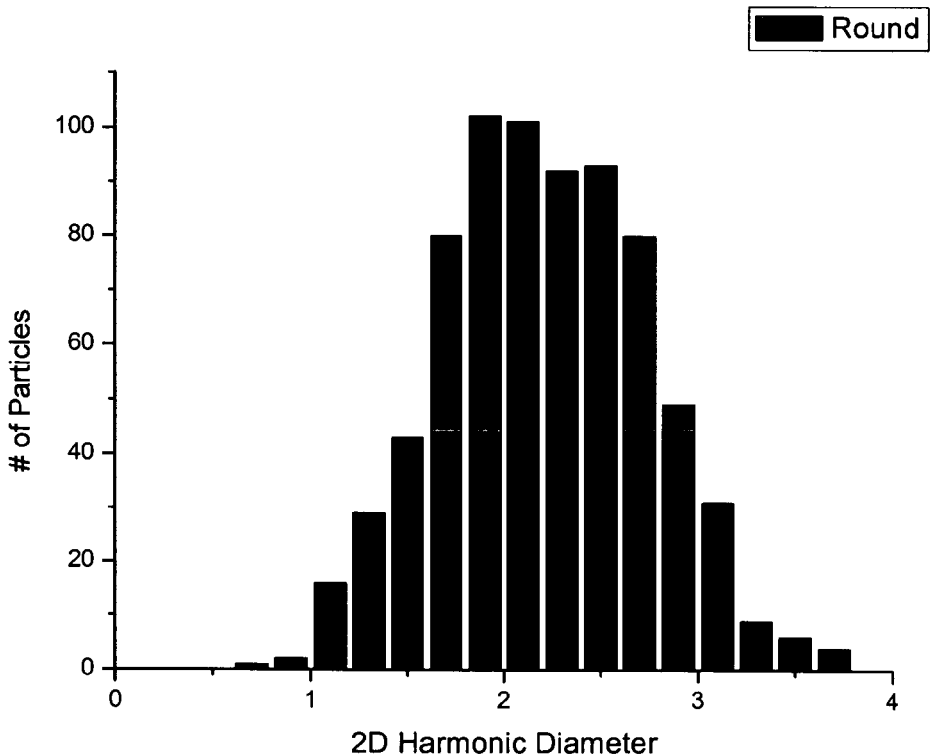
Figure 6C:
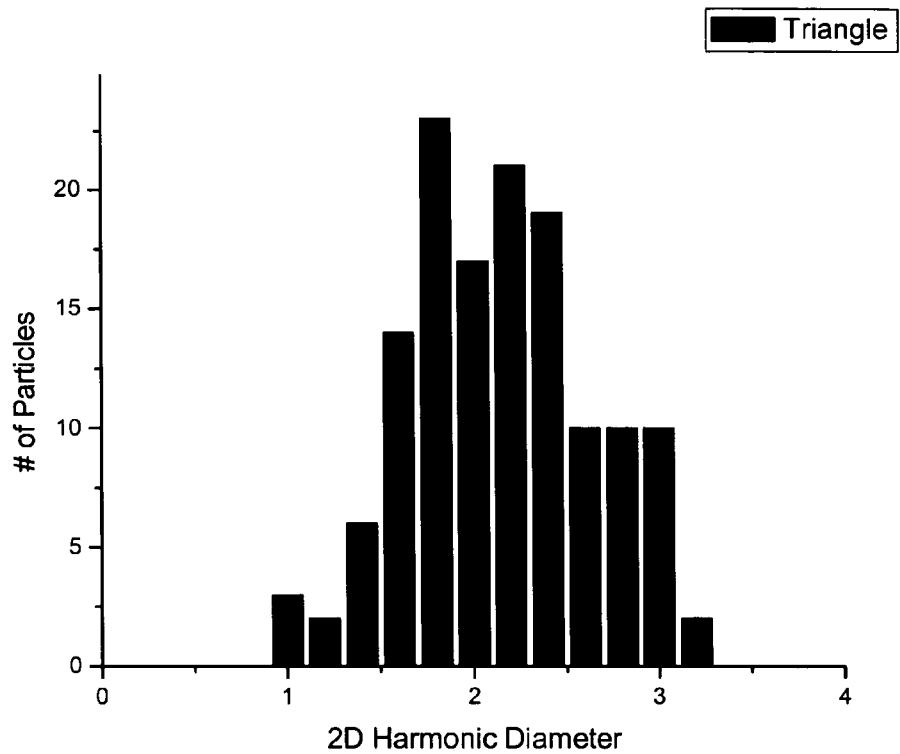
Figure 6D:
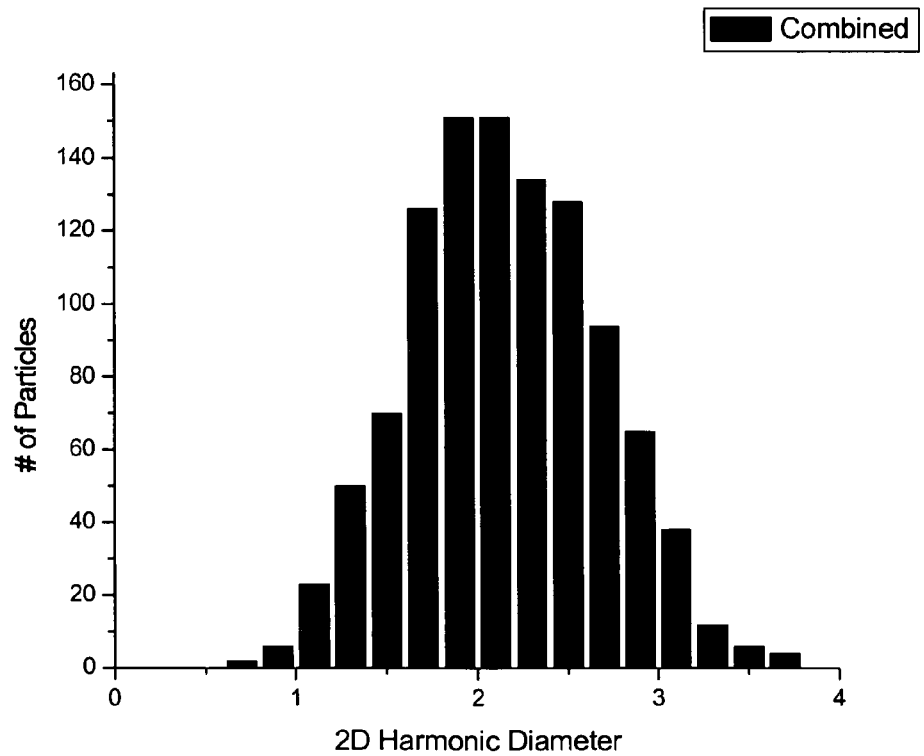
Figure 7A:
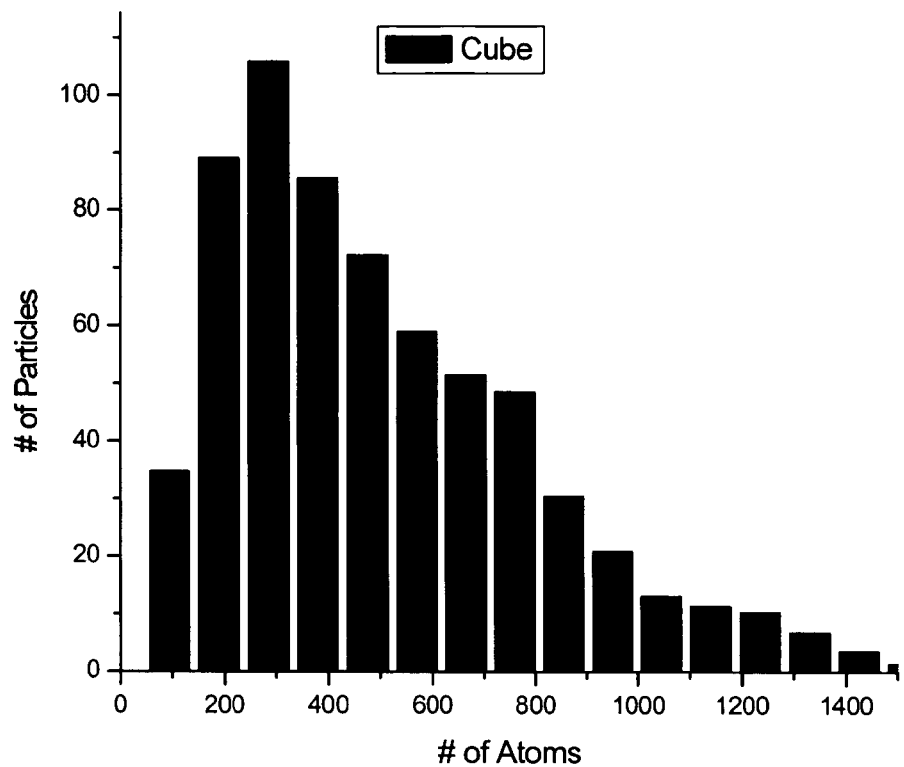
FIGS. 7A-D shows size distributions corresponding to 3D shapes.
Figure 7B:
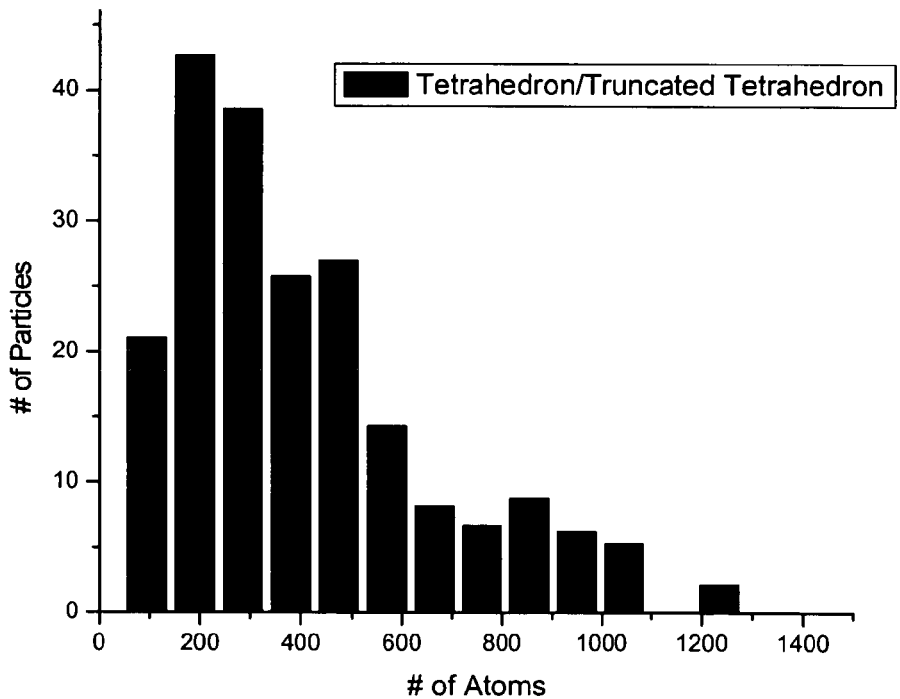
Figure 7C:
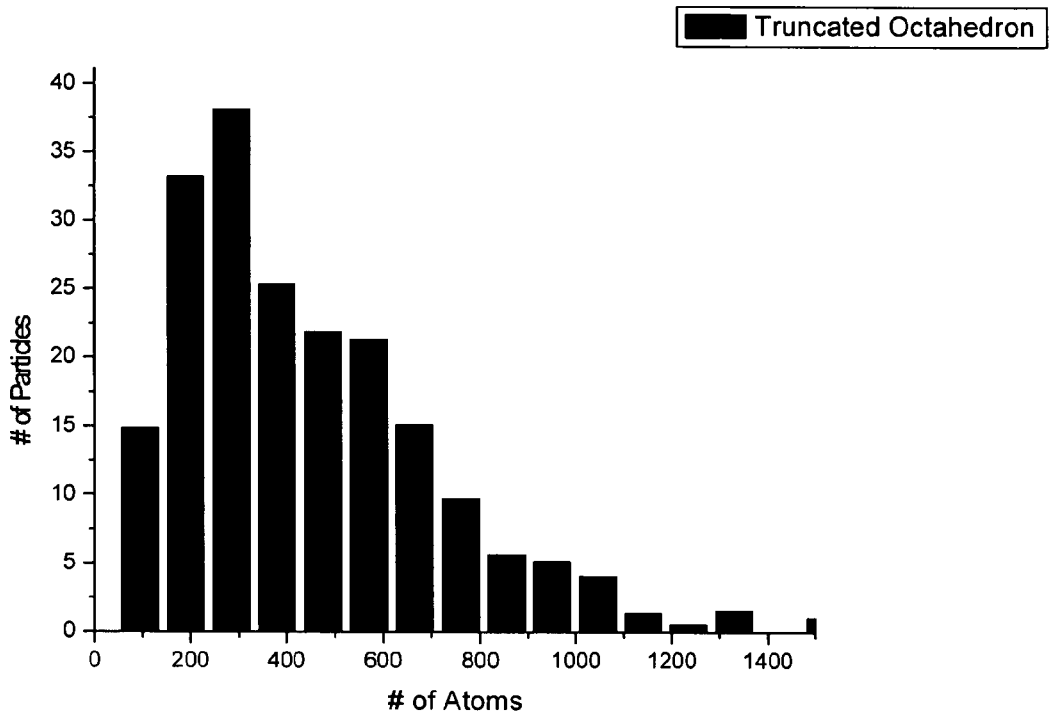

After the six distributions, g1(N), g2(N), g3(N), g4(N), g5(N) and g6(N), have been determined in discrete form in accordance with Steps 512-526, the solution to the equation $[CP']\times\{g\}$ is computed for each $N_L->N_U$ range to obtain $G_{cc}$, $G_{tt}$ and $G_{to}$ values for each $N_L->N_U$ range (Step 313). FIGS. 6A-6C show size distributions corresponding to 2D shapes for a batch of platinum nanoparticles, and FIGS. 7A-7C show size distributions corresponding to 3D shapes that were computed in the above manner. FIG. 6D shows the combined distribution of the size distributions corresponding to 2D shapes, and FIG. 7D shows the combined distribution of the size distributions corresponding to 3D shapes.

Figure 7D:
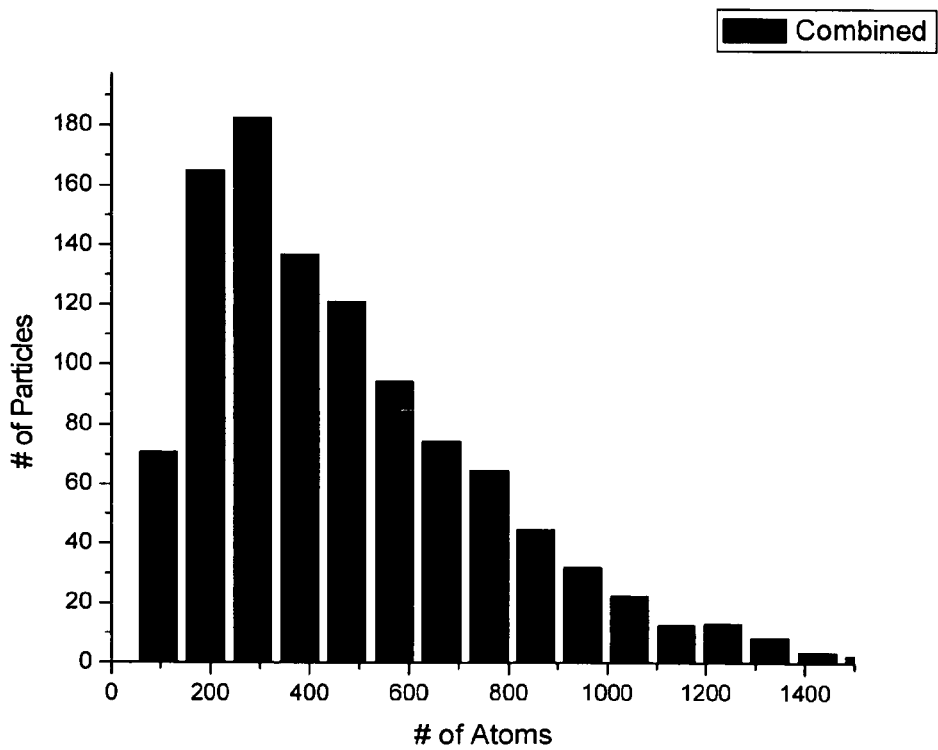
Figure 8:
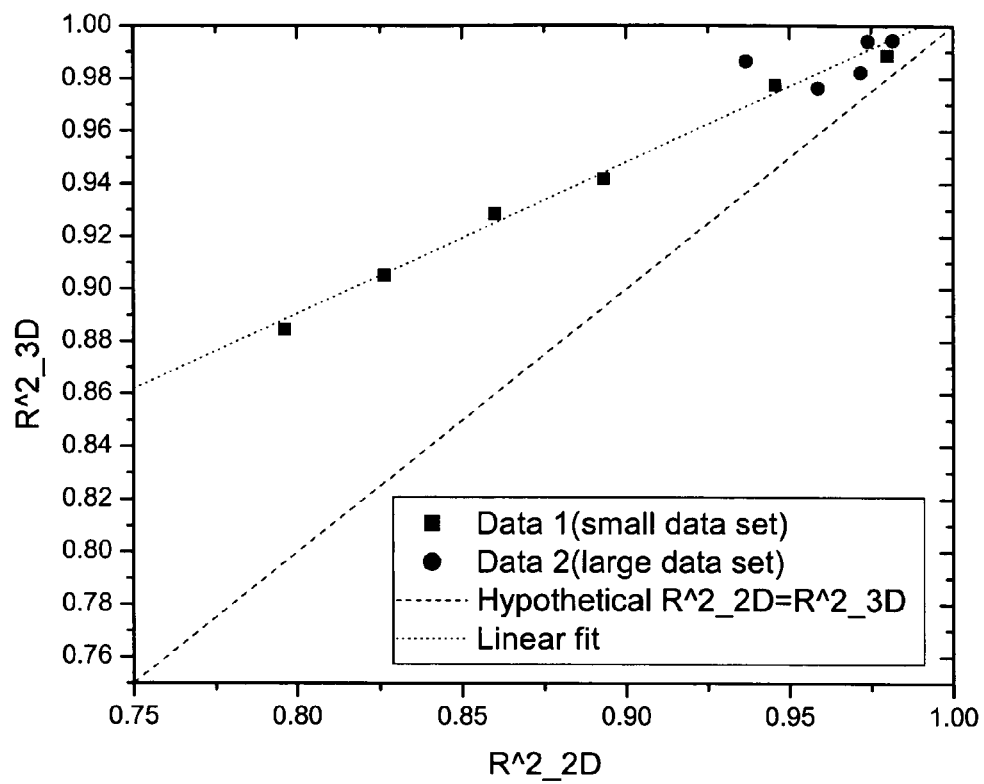
FIG. 8 graphically illustrates the goodness of log-normal fits for size distributions corresponding to 3D shapes and size distributions corresponding to 2D shapes.

The distribution shown in FIG. 7D provides a better log-normal distribution than the distribution shown in FIG. 6D, and this is an indication a more accurate model because, according to published literature, the size distribution of particles is expected to have a log-normal distribution. See, e.g., Kiss, L. B., et al., "New Approach to the Origin of Lognormal Size Distributions of Nanoparticles," Nanotechnology 10 (1999), pp. 25-28; and Granqvist, C. G., et al., "Ultrafine Metal Particles," Journal of Applied Physics, Vol. 47, No. 5 (May 1976), pp. 2200-2219. With the second embodiment of the present invention, the improvement in the log-normal distribution becomes more pronounced for smaller samples. FIG. 8 provides a comparison of the log-normal fit between size distributions determined using 2D shapes and size distributions determined using 3D shapes. It is shown that the improvement in the log-normal fit for small datasets (~100) is greater than for large datasets (~1000). This is noteworthy because nanoscale modeling that relies on log-normal size distributions, e.g., Monte Carlo simulations and atomistic simulations, becomes much easier and more practicable when smaller datasets are used.

In the 3D-to-2D projection matrix of FIG. 2, the relationships between various 2D shapes and various 3D shapes are defined by fixed values that were derived based on the probability of having a particle 2D projection among all possible projections of the 3D shapes. In the 3D-to-2D projection matrix of FIG. 9, the relationships between various 2D shapes and various 3D shapes do not become fixed until the variables, α1, α2, β1, β2 and β3, are assigned fixed values.

The variables, α1 and α2, have the following relationship: α2=1−α1. This is based on the observation that all particles having the 3D cube or cub-octahedron shape have either a 2D tetragon shape projection or a 2D round shape projection. The variables β1, β2 and β3, have the following relationship: β3=1−β1−β2. This is based on the observation that all particles having the 3D tetrahedron or truncated tetrahedron shape have a 2D tetragon shape projection or a 2D round shape projection or a 2D triangle or unique shape projection. The remaining three variables, α1, β1 and β2, take on numbers (from 0 to 1) that are randomly generated. Multiple sets of three numbers representing α1, β1 and β2 are randomly generated, and valid sets of α1, α2, β1, β2 and β3 are derived from the multiple sets and the above equations for α2 and β3.

Figure 10:
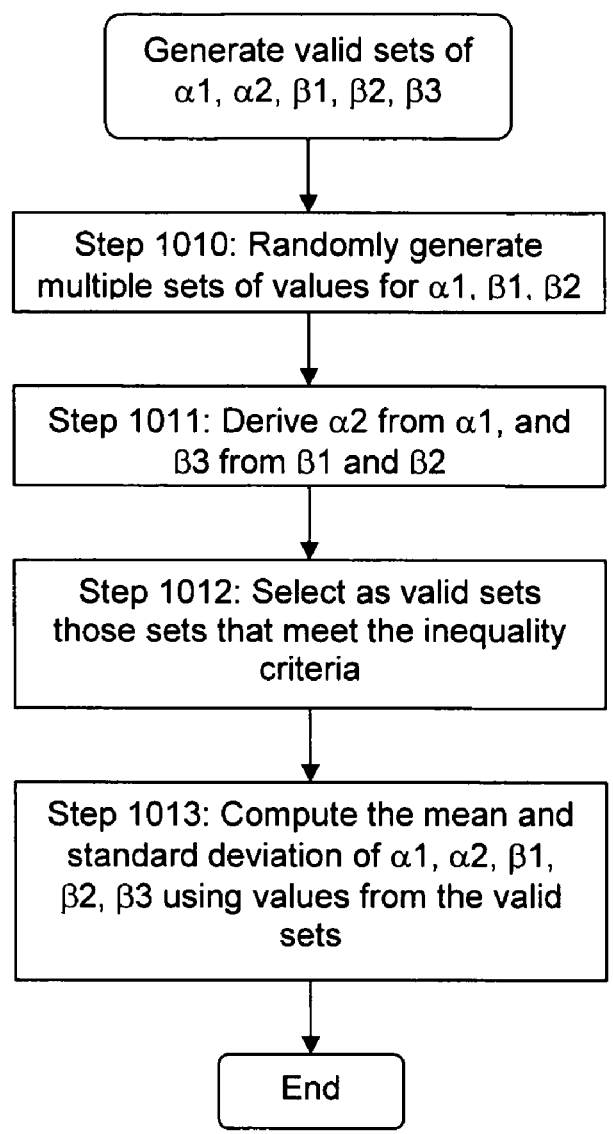
FIG. 10 is a flow diagram illustrating the method of determining sets of valid values for the variables that define the relationships between 2D shapes and 3D shapes.

In the method illustrated in FIG. 10, multiple sets of three numbers that range from 0 to 1, representing α1, β1 and β2, are randomly generated (Step 1010). In the embodiment illustrated herein, 10,000 sets are generated. Then, α2, which is equal to 1−α1, and β3, which is equal to 1−β1−β2, are computed for each of the sets, and added to the corresponding sets (Step 1011). In Step 1012, the sets that meet the following inequalities are selected as valid sets.

$$\frac{1}{\alpha_1} \times \left( M^{Tet} - \frac{\beta_1}{\beta_3} \times M^{Tri} \right) > 0;$$

and $$M^R - \frac{\alpha_2}{\alpha_1} \times M^{Tet} + \frac{\alpha_2}{\alpha_1} \times \frac{\beta_1}{\beta_3} - \frac{\beta_2}{\beta_3} \times M^{Tri} > 0,$$

where $M^{Tet}$, $M^R$ and $M^{Tri}$ are measured values for a particular nanoparticle batch and represent the number of nanoparticles having the 2D tetragon shape, 2D round shape and 2D triangle/unique shape, respectively. In Step 1013, the means and the standard deviations of α1, α2, β1, β2 and β3 are computed from the valid sets.

The method according to FIG. 10 was applied to two different nanoparticle batches, Pt62 and Pt63, and the results are tabulated below:

|  | Pt62 (applying the method of FIG. 10) | Pt63 (applying the method of FIG. 10) | Values based on the assumption of equal probability for all high-symmetry projections (used in the method according to FIG. 1 and FIG. 3) |
|---|---|---|---|
| <α1> | 0.58 | 0.60 | 0.34 |
| <α2> | 0.42 | 0.40 | 0.66 |
| <β1> | 0.21 | 0.18 | 0.09 |
| <β2> | 0.30 | 0.26 | 0.09 |
| <β3> | 0.49 | 0.56 | 0.82 |

| Pt62 (applying the method of FIG. 10) | Pt63 (applying the method of FIG. 10) | Values based on the assumption of equal probability for all high-symmetry projections (used in the method according to FIG. 1 and FIG. 3) |
|---|---|---|

A shape characterization method according to a third embodiment of the invention is identical to the first embodiment of the invention, except that the computed means values for α1, α2, β1, β2 and β3 are used instead of their theoretical values. The set of equations for deriving $M_{cc}$, $M_{tt}$ and $M_{to}$ is as follows:

$$M_{cc} = \frac{1}{<\alpha 1>}\left(M^{Tet} - \frac{<\beta 1>}{<\beta 3>}M^{Tri}\right)$$

$$M_{tt} = \frac{1}{<\beta 3>}M^{Tri}$$

$$M_{to} = M^R - \frac{<\alpha 2>}{<\alpha 1>}M^{Tet} + \left(\frac{<\alpha 2>}{<\alpha 1>} \times \frac{<\beta 1>}{<\beta 3>} - \frac{<\beta 2>}{<\beta 3>}\right)M^{Tri}$$

Figure 11:
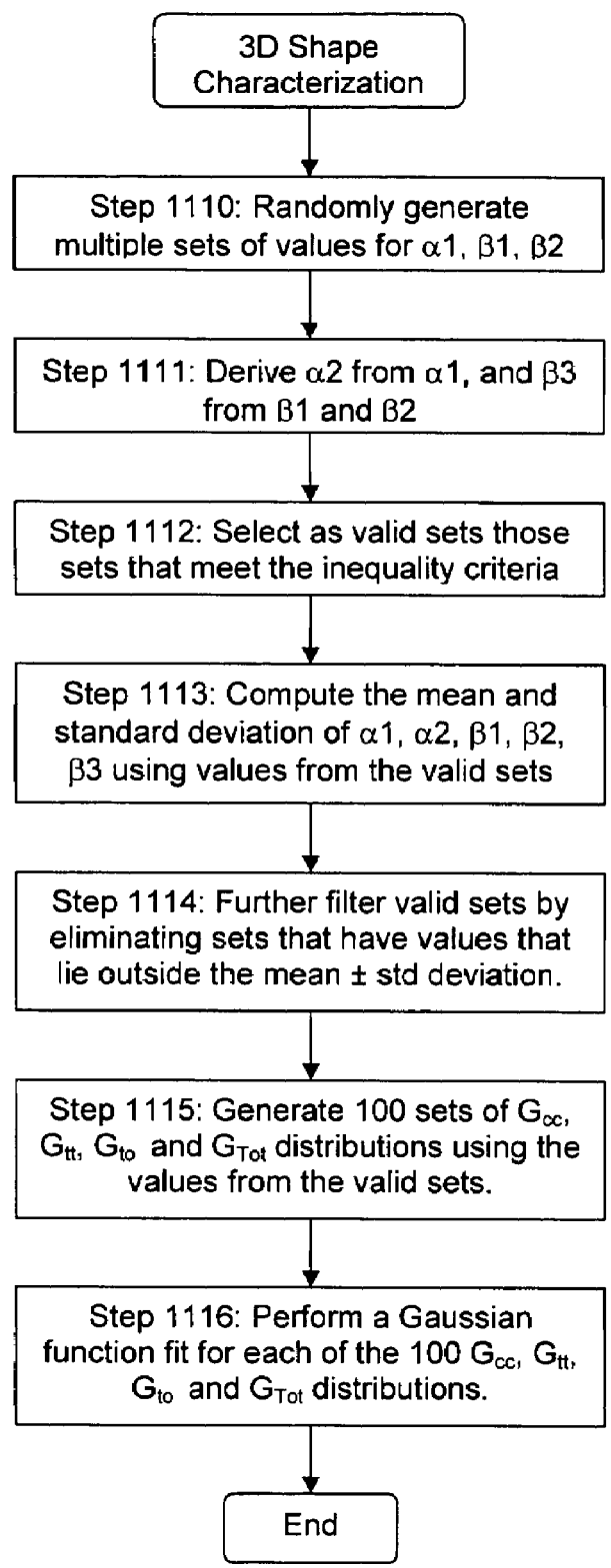
FIG. 11 is a flow diagram illustrating a shape characterization method according to a fourth embodiment of the invention.

A shape characterization method according to a fourth embodiment of the invention is illustrated in FIG. 11. Steps 1110-1113 of FIG. 11 are carried out identically as in Steps 1010-1013 of FIG. 10. In Step 1114, the valid sets are filtered by eliminating any set that has a number (α1, α2, β1, β2 or β3) that is not within the standard deviation of that number's corresponding mean. In other words, each of the remaining valid sets will have numbers, α1, α2, β1, β2 and β3, that satisfy the following criteria:

<α1>−SD(α1)<α1<<α1>+SD(α1);

<α2>−SD(α2)<α2<<α2>+SD(α2);

<β1>−SD(β1)<β1<<β1>+SD(β1);

<β2>−SD(β2)<β2<<β2>+SD(β2); and

<β3>−SD(β3)<β3<<β3>+SD)β3), where <X> represents the means of X and SD(X) represents the standard deviation of X.

In Step 1115, the shape characterization method according to the second embodiment of the invention is applied using the α1, 60 2, β1, β2 and β3 values of the valid sets to obtain a set of distributions including the 3D cc shape ($G_{cc}$) distribution, the 3D tt shape ($G_{tt}$) distribution, and the 3D to shape ($G_{to}$) distribution for every valid set. Step 1115 is carried out one valid set at a time until 100 valid sets, each of which generates $G_{cc}$, $G_{tt}$ and $G_{to}$ distributions that satisfy the following criteria, are identified:

0.1<($M_{cc}/M_{Tot}$)<0.9;

0.1<($M_{tt}/M_{Tot}$)<0.9; and 0.1<($M_{to}/M_{Tot}$)<0.9, where the upper and lower boundaries reflects the relative accuracy in the data of −10%; $M_{cc}$ represents the number of particles in the $G_{cc}$ distribution; $M_{tt}$ represents the number of particles in the $G_{tt}$ distribution; $M_{to}$ represents the number of particles in the $G_{to}$ distribution; and $M_{Tot}=M_{cc}+M_{tt}+M_{to}$.

Figure 12A:
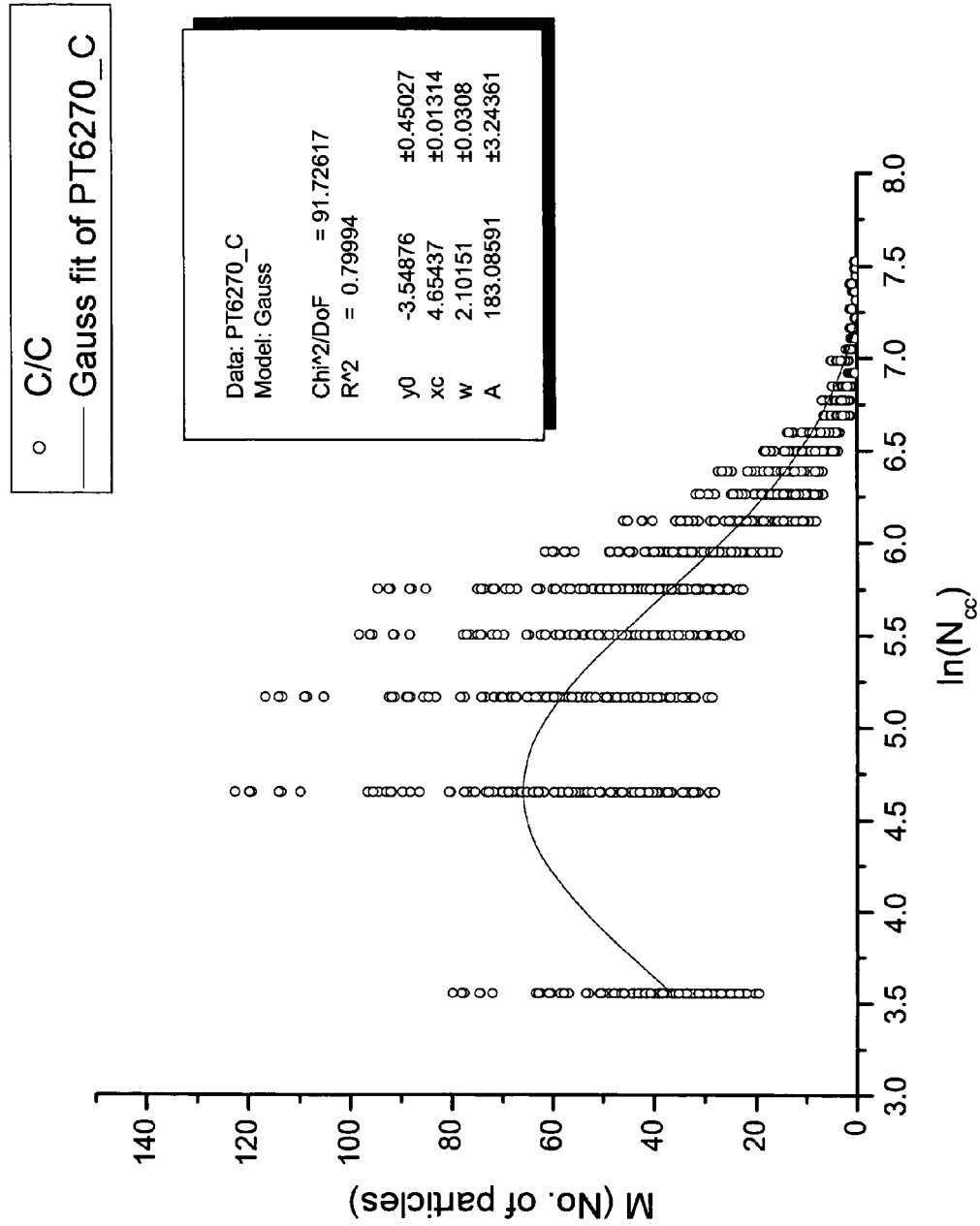
FIGS. 12A-D shows size distributions corresponding to 3D shapes for a first nanoparticle batch as derived according to the shape characterization method of FIG. 11.
Figure 12B:
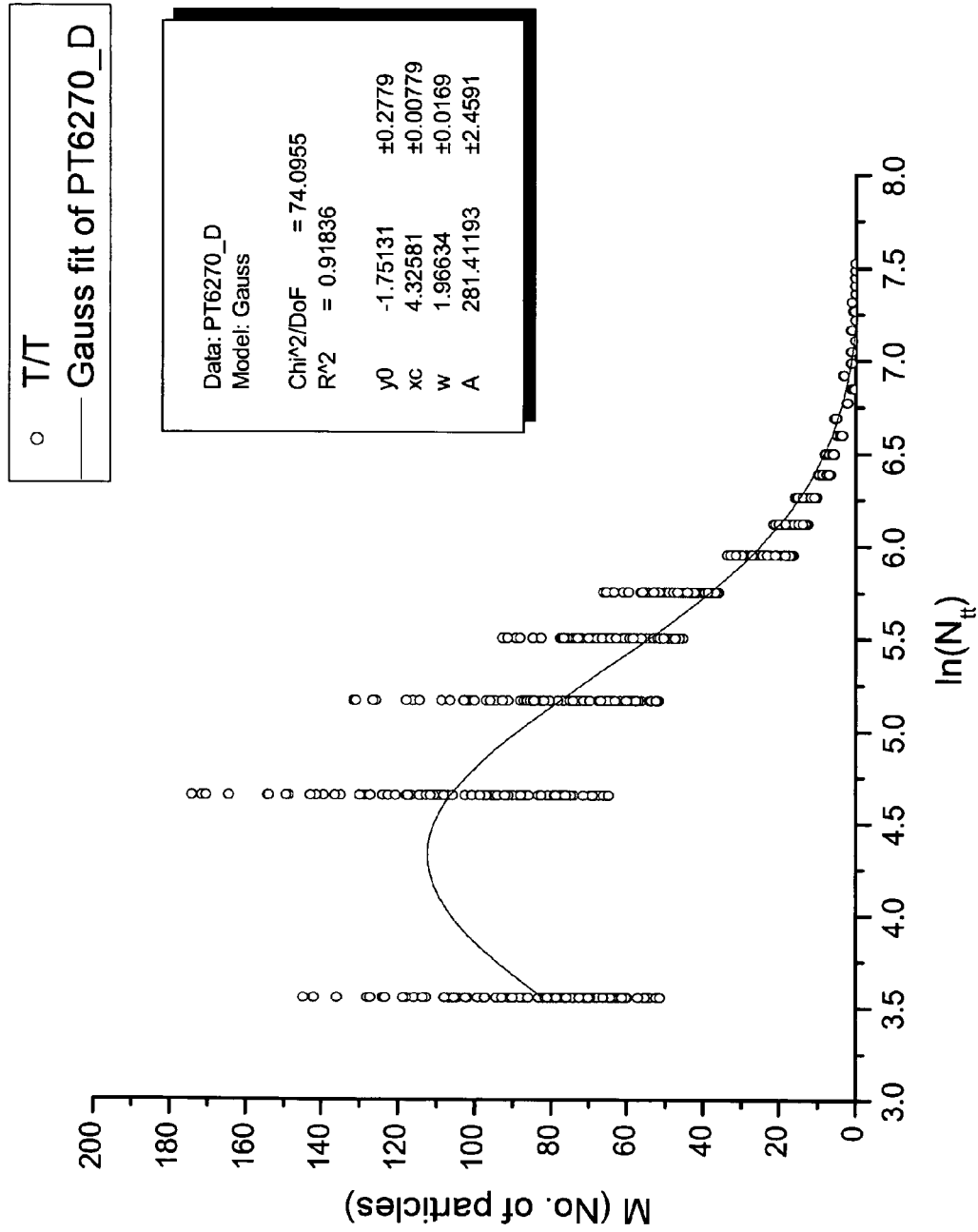
Figure 12C:
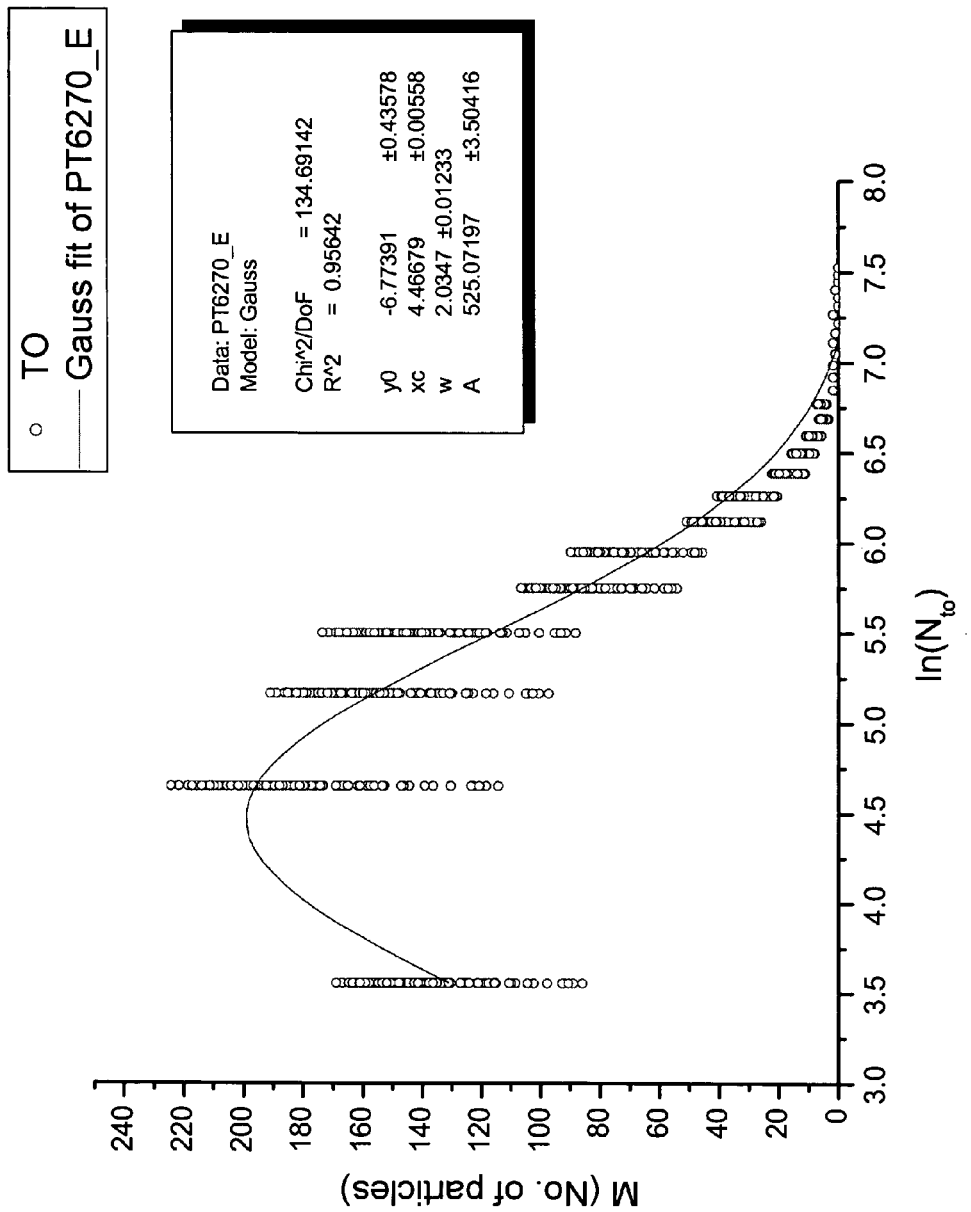
Figure 12D:
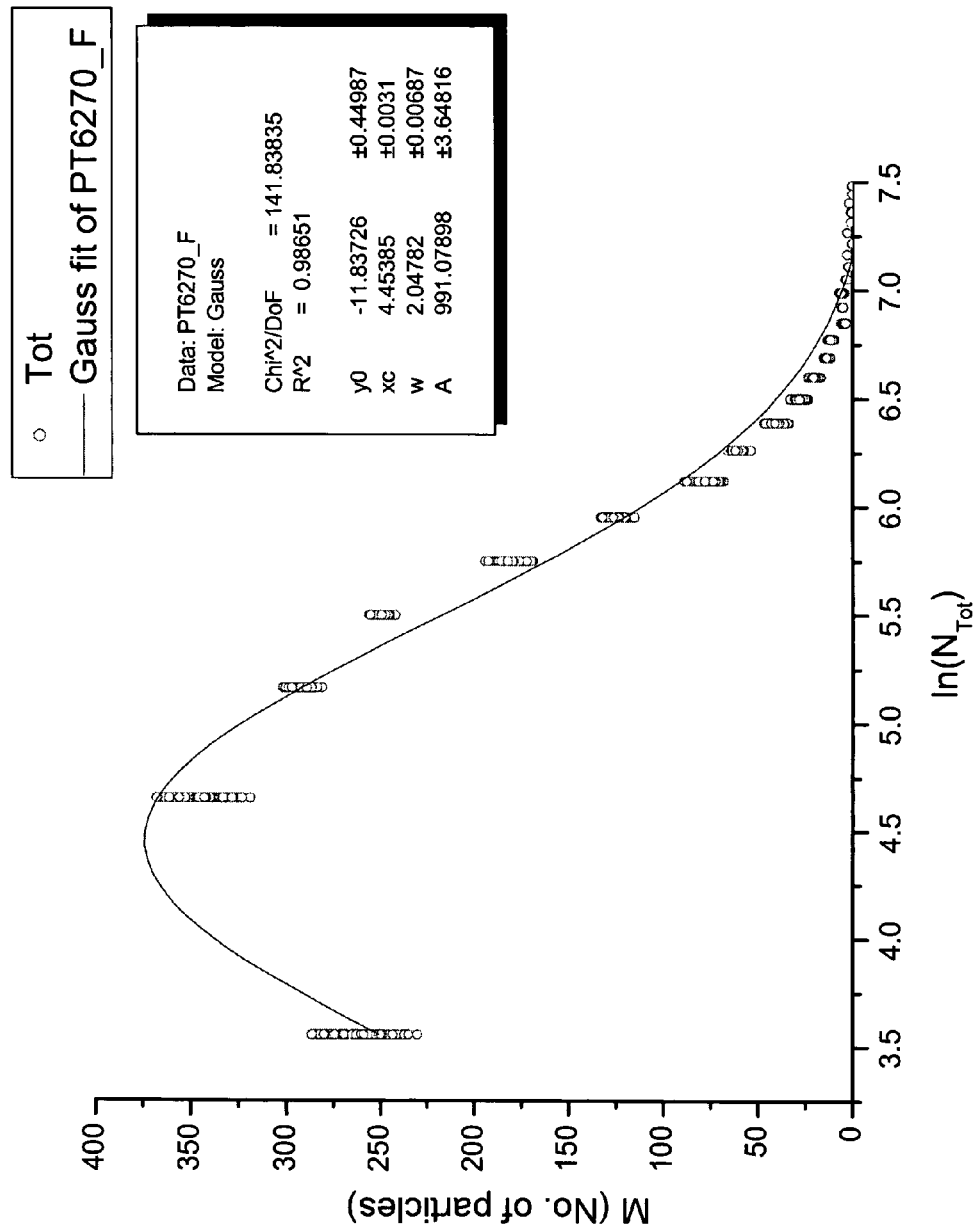
Figure 13A:
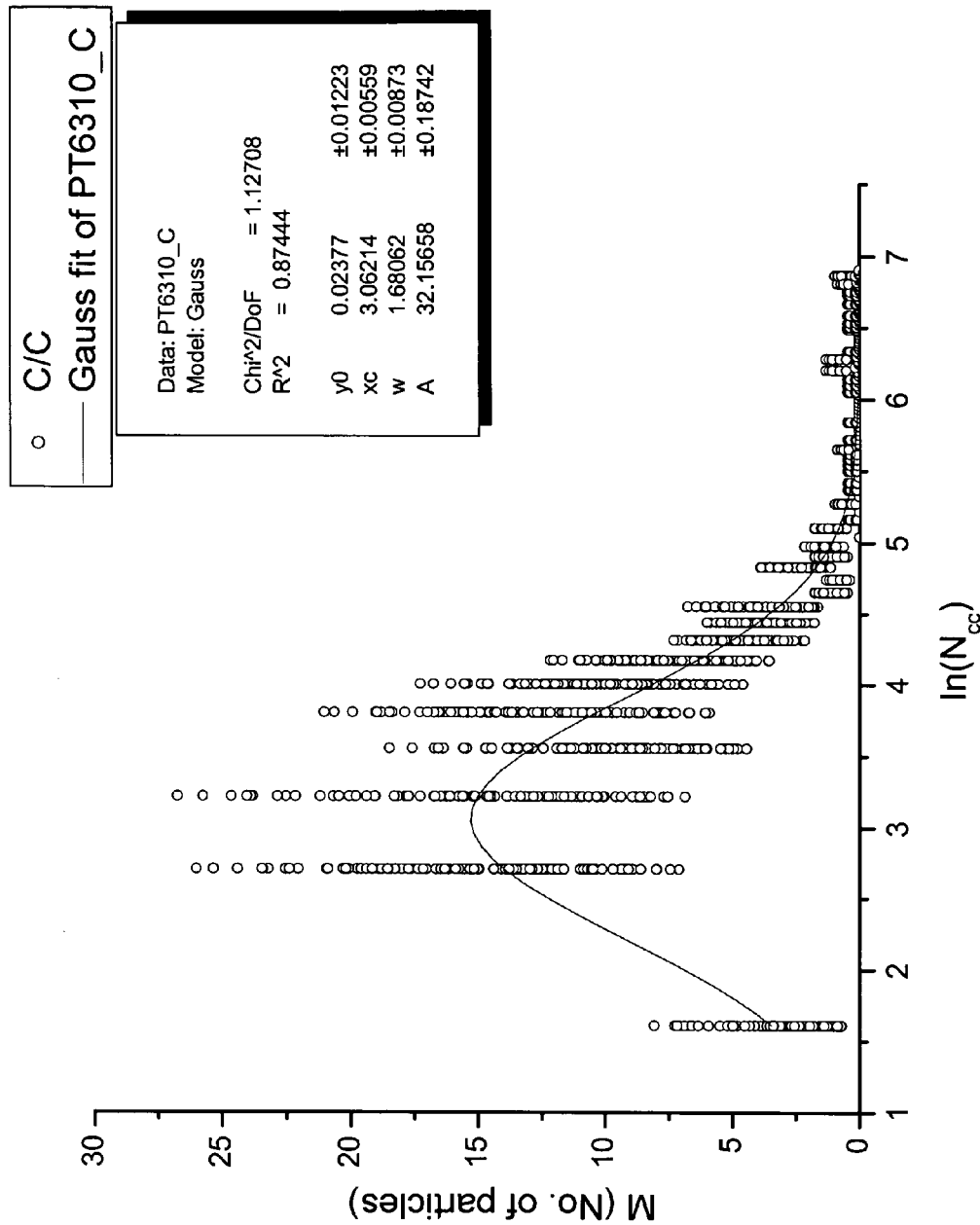
FIGS. 13A-D shows size distributions corresponding to 3D shapes for a second nanoparticle batch as derived according to the shape characterization method of FIG. 11.
Figure 13B:
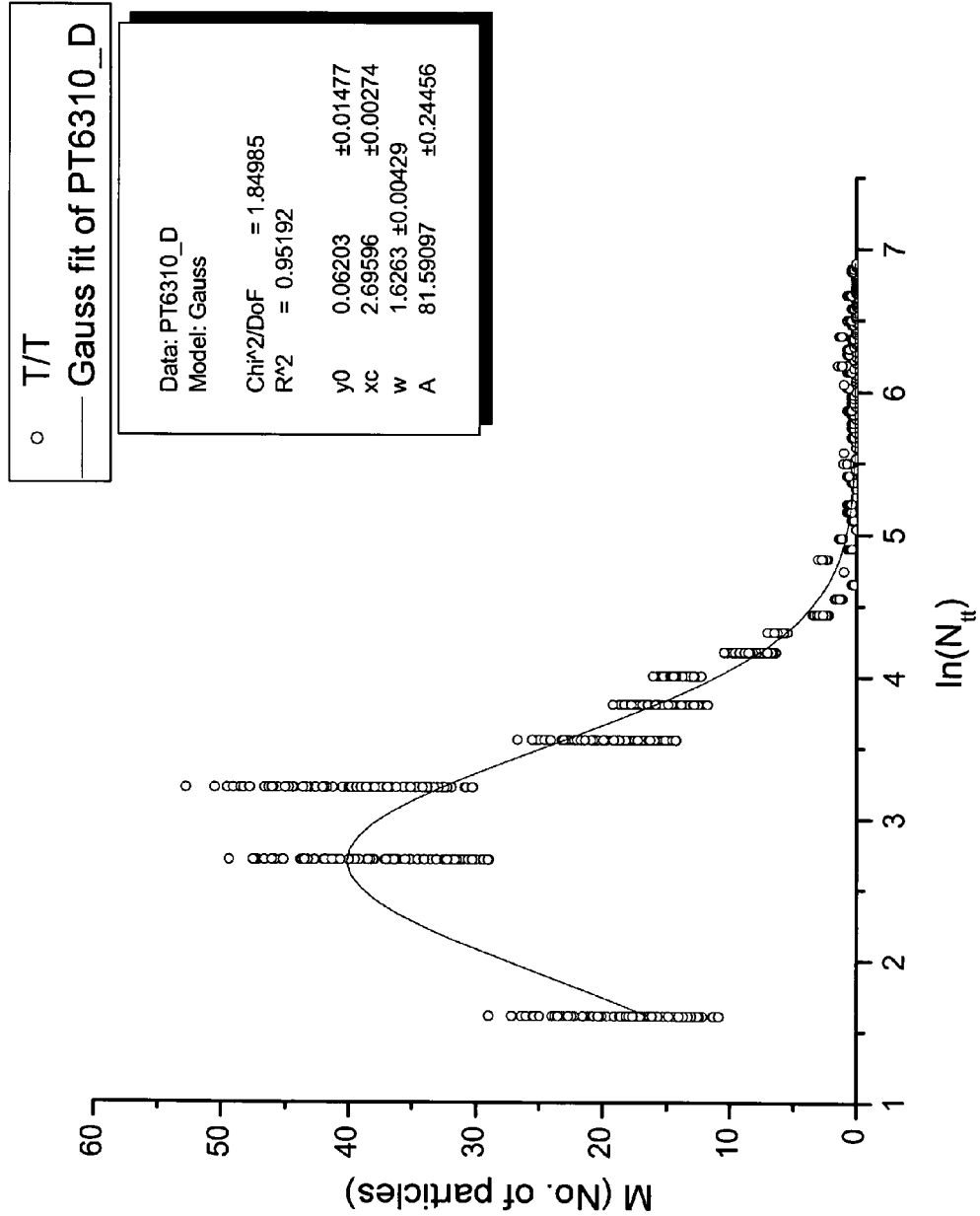
Figure 13C:
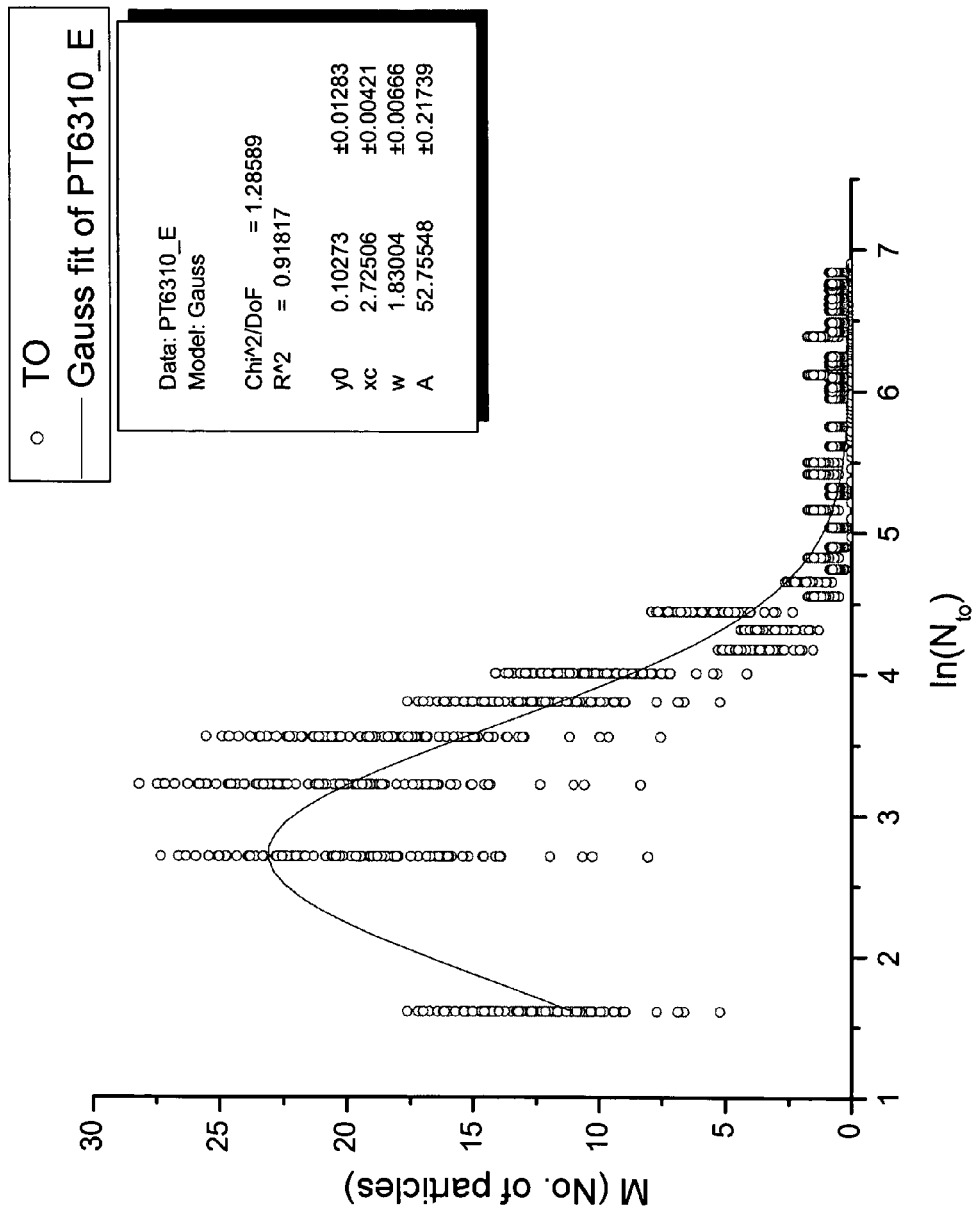
Figure 13D:
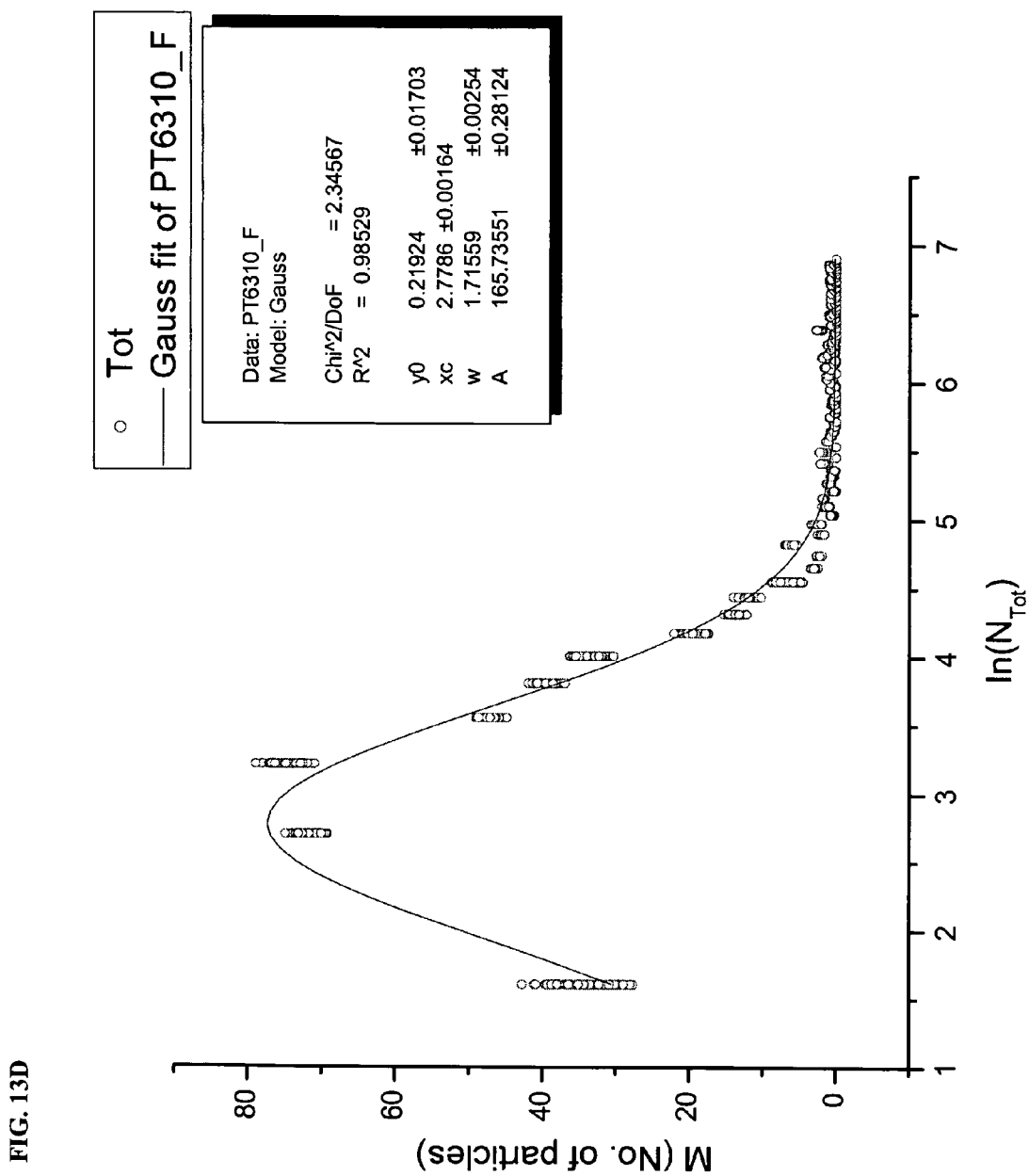

The 100 $G_{cc}$, $G_{tt}$ and $G_{to}$ distributions that were generated from the 100 valid sets may be plotted against N, the number of atoms, or against ln(N). The plots of the 100 $G_{cc}$, $G_{tt}$ and $G_{to}$ distributions shown with respect to ln(N) are illustrated in FIGS. 12A-C. FIG. 12D represents the combined $G_{cc}$, $G_{tt}$ and $G_{to}$ distributions, referred to as $G_{Tot}$, plotted against ln(N). FIGS. 12A-D represent size distributions corresponding to 3D shapes for the Pt62 nanoparticle batch. FIGS. 13A-D represent size distributions corresponding to 3D shapes for the Pt63 nanoparticle batch.

The number of particles, $M_{cc}$, $M_{tt}$, $M_{to}$ and $M_{Tot}$ for the Pt62 nanoparticle batch and the Pt63 nanoparticle batch, as determined from the $G_{cc}$, $G_{tt}$ and $G_{to}$ distributions, are tabulated below. The table shows that the total number of particles, $M_{Tot}$, as modeled, compares well with the total number of particles that were counted from the TEM image ($M^{Tet}+M^{R}+M^{Tri}$).

| Batch | $M_{cc}$ | $M_{tt}$ | $M_{to}$ | $M_{Tot}$ | $M^{Tet} + M^R + M^{Tri}$ |
|---|---|---|---|---|---|
| Pt62 | 365 | 453 | 908 | 1726 | 1727 |
| Pt63 | 100 | 175 | 136 | 411 | 410 |

In Step 1116, the 100 $G_{cc}$(ln(N)), $G_{tt}$(ln(N)), $G_{to}$(ln(N)) and $G_{Tot}$(ln(N)) distributions for both nanoparticle batches, Pt62 and Pt63, are fitted with a Gaussian function. The results of the Gaussian fit are tabulated below:

| Batch | $G_{cc}\mu$ | $G_{cc}\sigma$ | $G_{tt}\mu$ | $G_{tt}\sigma$ | $G_{to}\mu$ | $G_{to}\sigma$ | $G_{Tot}\mu$ | $G_{Tot}\sigma$ |
|---|---|---|---|---|---|---|---|---|
| Pt62 | 4.6544 | 1.0507 | 4.3258 | 0.9831 | 4.4668 | 1.0173 | 4.4539 | 1.0239 |
| Pt63 | 3.0621 | 0.8403 | 2.6960 | 0.8131 | 2.7251 | 0.9150 | 2.7786 | 0.8578 |

The corresponding log-normal distribution is $$G^{LN1}(N) = \frac{1}{\sqrt{2\pi}\ln(\sigma)} \times \exp\left(-\frac{(\ln(N) - \ln(\mu))^2}{2\ln^2\sigma}\right)$$

An alternative form of the log-normal distribution is $$G^{LN2}(N) = \frac{1}{\sqrt{2\pi}\,SN} \times \exp\left(-\frac{(\ln(N) - M)^2}{2S^2}\right)$$

where M and S are 0.42, 0.34 and −0.17, 0.29 for Pt62 and Pt63, respectively. Knowing M and S; all statistical moments can be calculated for the corresponding distribution.

The 3D-to-2D projection matrix of FIG. 9 may be expanded to provide relationships between six different 2D shape classes and six different 3D shape classes. The six different 2D shape classes include one 2D shape class for each of triangle, square, rectangle, round, rhombus, and unique. The six different 3D shape classes include one 3D shape class for each of tetrahedron, cube, octahedron, truncated tetrahedron, cub-octahedron, and truncated octahedron. The possible projections of the 3D shapes from the six 3D shape classes into one or more of the 2D shapes from the six different 2D shape classes are illustrated in FIG. 14, and the relationships between them are defined by variables $\alpha 1$, $\alpha 2$, $\beta 2$, $\beta 3$, $\beta 4$, $X2$, $X3$, $X4$, $X5$, $\delta 4$, $\delta 6$, $\epsilon 2$, $\epsilon 4$, and $\phi 4$. The relationships between the 3D shapes and the 2D shapes do not become fixed until the variables, $\alpha 1$, $\alpha 2$, $\beta 2$, $\beta 3$, $\beta 4$, $X2$, $X3$, $X4$, $X5$, $\delta 4$, $\delta 6$, $\epsilon 2$, $\epsilon 4$, and $\phi 4$, are assigned fixed values.

The variables, $\alpha 1$ and $\alpha 2$, have the following relationship: $\alpha 2 = 1 - \alpha 1$. This is based on the observation that all particles having the 3D tetrahedron shape have either a 2D triangle shape projection or a 2D square shape projection. The variables, $\beta 2$, $\beta 3$ and $\beta 4$, have the following relationship: $\beta 4 = 1 - \beta 2 - \beta 3$. This is based on the observation that all particles having the 3D cube shape have a 2D square shape projection or a 2D rectangle shape projection or a 2D round shape projection. The variables, $X2$, $X3$, $X4$ and $X5$, have the following relationship: $X5 = 1 - X2 - X3 - X4$. This is based on the observation that all particles having the 3D octahedron shape have a 2D square shape projection or a 2D rectangle shape projection or a 2D round shape projection or a 2D rhombus shape projection. The variables, $\delta 4$ and $\delta 6$, have the following relationship: $\delta 6 = 1 - \delta 4$. This is based on the observation that all particles having the 3D truncated tetrahedron shape have either a 2D round shape projection or a 2D unique shape projection. The variables, $\epsilon 2$ and $\epsilon 4$, have the following relationship: $\epsilon 4 = 1 - \epsilon 2$. This is based on the observation that all particles having the 3D cub-octahedron shape have either a 2D square shape projection or a 2D round shape projection. The variable, $\phi 4$, is equal to one. This is based on the observation that all particles having the 3D truncated octahedron shape have only a 2D round shape projection.

The independent variables, $\alpha 1$, $\beta 2$, $\beta 3$, $X2$, $X3$, $X4$, $\delta 4$ and $\epsilon 2$, take on numbers (from 0 to 1) that are randomly generated. Multiple sets (e.g., 10,000) of eight numbers representing $\alpha 1$, $\beta 2$, $\beta 3$, $X2$, $X3$, $X4$, $\delta 4$ and $\epsilon 2$ are randomly generated, and for each set, the values for the dependent variables, $\alpha 2$, $\beta 4$, $X5$, $\delta 6$ and $\epsilon 4$ are derived from the randomly generated values for the independent variables and are added to the set. The value for $\phi 4$, which is always equal to one, is also added to each of the multiple sets. Then, the sets that meet the following inequalities are selected as valid sets.

$$\frac{1}{\beta 3} \times \left( M3 - \frac{\chi^3}{\chi^5} \times M5 \right) > 0;$$

$$\frac{1}{\varepsilon 2} \times \left[ M2 - \frac{\alpha 2}{\alpha 1} \times M1 - \frac{\beta 2}{\beta 3} \times \left( M3 - \frac{\chi^3}{\chi^5} \times M5 \right) - \frac{\chi^2}{\chi^5} \times M5 \right] > 0;$$

and $$\frac{1}{\phi 4} \times \left[ M4 - \frac{\beta 4}{\beta 3} \times \left( M3 - \frac{\chi^3}{\chi^5} \times M5 \right) - \frac{\chi^4}{\chi^5} \times M5 - \frac{\delta 4}{\delta 6} \times M6 - \frac{\varepsilon 4}{\varepsilon 2} \times \left( M2 - \frac{\alpha 2}{\alpha 1} \times M1 - \frac{\beta 2}{\beta 3} \times \left( M3 - \frac{\chi^3}{\chi^5} \times M5 \right) - \frac{\chi^2}{\chi^5} \times M5 \right) \right] > 0,$$

where M1=number of triangles; M2=number of squares; M3=number of rectangles; M4=number of rounds; M5=number of rhombi; and M6=number of uniques. Then, the means of $\alpha 1$, $\alpha 2$, $\beta 2$, $\beta 3$, $\beta 4$, $X2$, $X3$, $X4$, $X5$, $\delta 4$, $\delta 6$, $\epsilon 2$, $\epsilon 4$, and $\phi 4$ are computed from the valid sets. The means of $\alpha 1$, $\alpha 2$, $\beta 2$, $\beta 3$, $\beta 4$, $X2$, $X3$, $X4$, $X5$, $\delta 4$, $\delta 6$, $\epsilon 2$, $\epsilon 4$, and $\phi 4$, as computed from valid sets of two different nanoparticle batches, Pt62 and Pt63, are tabulated below:

|  | Pt62 | Pt63 | Values based on equal probability for all high-symmetry projections |
|---|---|---|---|
| $<\alpha 1>$ | 0.77 | 0.71 | 0.84 |
| $<\alpha 2>$ | 0.23 | 0.28 | 0.16 |
| $<\beta 2>$ | 0.04 | 0.26 | 0.23 |
| $<\beta 3>$ | 0.63 | 0.44 | 0.46 |
| $<\beta 4>$ | 0.33 | 0.30 | 0.31 |
| $<\chi 2>$ | 0.08 | 0.20 | 0.20 |
| $<\chi 3>$ | 0.29 | 0.17 | 0.26 |
| $<\chi 4>$ | 0.25 | 0.23 | 0.27 |
| $<\chi 5>$ | 0.38 | 0.40 | 0.27 |
| $<\delta 4>$ | 0.36 | 0.26 | 0.20 |
| $<\delta 6>$ | 0.64 | 0.74 | 0.80 |
| $<\epsilon 2>$ | 0.51 | 0.60 | 0.12 |
| $<\epsilon 4>$ | 0.49 | 0.40 | 0.88 |
| $<\phi 4>$ | 1.00 | 1.00 | 1.00 |

While particular embodiments according to the invention have been illustrated are described above, those skilled in the art understand that the invention can take a variety of forms and embodiments within the scope of the appended claims.

What is claimed is:

1. A method of estimating 3D shape distributions of particles, comprising the steps of:
    defining variable relationships between 2D shapes and 3D shapes;
    generating multiple sets of numbers, wherein the numbers in each of the multiple sets fix the variable relationships between the 2D shapes and the 3D shapes, wherein each of the multiple sets includes five numbers, and three of the five numbers, $\alpha 1$, $\beta 1$, $\beta 2$, in each of the multiple sets are randomly generated, and the remaining two of the five numbers are derived using the following equations: $\alpha 2 = 1 - \alpha 1$, and $\beta 3 = 1 - \beta 1 - \beta 2$;
    selecting a number of sets from the multiple sets; and
    estimating the 3D shape distributions of the particles based on the selected sets.

2. The method according to claim 1, further comprising the step of determining the number of 2D tetragon shapes, M1, the number of 2D round shapes, M2, and number of 2D triangle or unique shapes, M3 in the particles, wherein the numbers in each of the selected sets satisfy the following inequalities: $(1/\alpha 1)*[M1-(\beta 1/\beta 3)*M3]>0$, and $M2-(\alpha 2/\alpha 1)*M1+(\alpha 2/\alpha 1)*(\beta 1/\beta 3)-(\beta 2/\beta 3)*M3>0$.

3. A method of estimating a distribution of nanoparticles based on a matrix for mapping at least three 2D shapes onto at least three 3D shapes, comprising the steps of:
    establishing matrix variables that define the relationships between the 2D shapes and the 3D shapes;
    generating multiple sets of numbers, wherein the numbers in each of the multiple sets are assigned to the matrix variables to fix the relationships between the 2D shapes and the 3D shapes, wherein each set defines five numbers, $\alpha 1$, $\alpha 2$, $\beta 1$, $\beta 2$, $\beta 3$; computing the mean and the standard deviation for each of the numbers, $\alpha 1$, $\alpha 2$, $\beta 1$, $\beta 2$, $\beta 3$;
    selecting those sets whose numbers all lie within their computed mean ± computed standard deviation; and generating a distribution corresponding to a first 3D shape based on the matrix and the numbers in the selected sets.

4. The method according to claim 3, further comprising the step of generating a distribution corresponding to a second 3D shape based on the matrix and the numbers in the selected sets.

5. The method according to claim 4, further comprising the step of generating a distribution corresponding to a third 3D shape based on the matrix and the numbers in the selected sets.

6. The method according to claim 5, further comprising the step of determining the total number of nanoparticles, M, wherein the selected sets do not include any set for which the distributions of the 3D shapes are such that: the total number of nanoparticles having the first 3D shape is less than 10%*M or greater than 90%*M; or the total number of nanoparticles having the second 3D shape is less than 10%*M or greater than 90%*M; or the total number of nanoparticles having the third 3D shape is less than 10%*M or greater than 90%*M.

* * * * *